United States Patent
Shu et al.

(10) Patent No.: US 7,115,393 B2
(45) Date of Patent: Oct. 3, 2006

(54) MELANOCORTIN-1 RECEPTOR AND METHODS OF USE

(75) Inventors: Youmin Shu, Potomac, MD (US);
Xuan Li, Silver Spring, MD (US);
Anthony C. Yee, Adelphi, MD (US);
Gilbert Jay, North Bethesda, MD (US)

(73) Assignee: OriGene Technologies, Inc., Rockville, MD (US)

( * ) Notice: Subject to any disclaimer, the term of this patent is extended or adjusted under 35 U.S.C. 154(b) by 278 days.

(21) Appl. No.: 10/164,717

(22) Filed: Jun. 10, 2002

(65) Prior Publication Data

US 2003/0228658 A1    Dec. 11, 2003

(51) Int. Cl.
*C07K 14/72*    (2006.01)
*C12N 15/12*    (2006.01)

(52) U.S. Cl. .................. 435/69.1; 536/23.5; 530/300; 530/350; 435/320.1; 435/325

(58) Field of Classification Search ............... 536/23.1, 536/23.5, 24.3; 530/350, 300; 435/69.1
See application file for complete search history.

(56) References Cited

U.S. PATENT DOCUMENTS 6,693,184 B1 * 2/2004 Howard et al.

FOREIGN PATENT DOCUMENTS

WO    WO 200039147 A1 * 7/2000

OTHER PUBLICATIONS

Mundy et al., Evolution of a pigmentation gene, the melanocrotin-1 receptor, in primates, Am. J. Phys. Anthr. 121:67-80, 2003.*
Sturm et al., Human pigmentation genes:identification, structure and consequences of polymorphic variation, Gene 277:49-62, 2001.*
NCBI Online Mendelian Inheritance in Man (OMIM) database, MIM 155555, "Melanocortin 1 Receptor; MC1R", created Nov. 3, 1992, last updated Oct. 5, 2005.*
Valverde et al., Variants of the melanocyte-stimulating hormone receptor gene are associated with red hair and fair skin in humans, Nat. Genet. 11(3):328-330, Nov. 1995.*

* cited by examiner

*Primary Examiner*—Lorraine Spector
*Assistant Examiner*—Claire M. Kaufman
(74) *Attorney, Agent, or Firm*—Millen, White, Zelano & Branigan, P.C.

(57) ABSTRACT

The present invention relates to all facets of novel polynucleotides for melanocortin-1 receptors, the polypeptides they encode, antibodies and specific binding partners thereto, and their applications to research, diagnosis, drug discovery, therapy, clinical medicine, forensic science and medicine, etc. The polynucleotides are useful in variety of ways, including, but not limited to, as molecular markers, as drug targets, and for detecting, diagnosing, staging, monitoring, prognosticating, preventing or treating, determining predisposition to, etc., diseases and conditions especially relating to melanocortin-1, such as melanoma, pigmentation disorders and conditions, inflammation, etc.

14 Claims, 2 Drawing Sheets

```
              *        20         *        40         *        60
NM_002386 : MAVQGSQRRLLGSLNSTPTAIPQLGLAANQTGARCLEVSISDGLELSIGLVSLVENALVV : 60
MC-1RC    : MAVQGSQRRLLGSLNSTPTAIPQLGLAANQTGARCLEVSISDGLFLSIGLVSLVENALVV : 60
MC-1RB    : MAVQGSQRRLLGSLNSTPTAIPQLGLAANQTGARCLEVSISDGLFLSIGLVSLVENALVV : 60

*        80         *       100         *       120
NM_002386 : ATIAKNRNLHSPMYCFICCLALSDLLVSGSNVLETAVILLLEAGALVARAAVLQQLDNVT : 120
MC-1RC    : ATIAKNRNLHSPMYCFICCLALSDLLVSGSNVLETAVILLLEAGALVARAAVLQQLDNVT : 120
MC-1RB    : ATIAKNRNLHSPMYCFICCLALSDLLVSGSNVLETAVILLLEAGALVARAAVLQQLDNVT : 120

*       140         *       160         *       180
NM_002386 : DVITCSSMLSSLCFLGAIAVDRYISIFYALRYHSIVTLPRARQAVAAIWVASVVFSTLFI : 180
MC-1RC    : DVITCSSMLSSLCFLGAIAVDRYISIFYALRYHSIVTLPRARRAVAAIWVASVVFSTLFI : 180
MC-1RB    : DVITCSSMLSSLCFLGAIAVDRYISIFYALRYHSIVTLPRARRAVAAIWVASVVFSTLFI : 180

*       200         *       220         *       240
NM_002386 : AYYDHVAVLLCLVVFFLAMLVLMAVLYVHMLARACQHAQGIARLHKRQRPVHQGFGLKGA : 240
MC-1RC    : AYYDHVAVLLCLVVFFLAMLVLMAVLYVHMLARACQHAQGIARLHKRQRPVHQGFGLKGA : 240
MC-1RB    : AYYDHVAVLLCLVVFFLAMLVLMAVLYVHMLARACQHAQGIARLHKRQRPVHQGFGLKGA : 240

*       260         *       280         *       300
NM_002386 : VTLTILLGIFFLCWGPFFLHLTLIVLCPEHPTCGCIFKNFNLFLALIICNAIIDPLIYAF : 300
MC-1RC    : VTLTILLGIFFLCWGPFFLHLTLIVLCPEHPTCGCIFKNFNLFLALIICNAIIDPLIYAF : 300
MC-1RB    : VTLTILLGIFFLCWGPFFLHLTLIVLCPEHPTCGCIFKNFNLFLALIICNAIIDPLIYAF : 300

*       320         *       340         *       360
NM_002386 : HSQELRRTLKEVLTCSW-------------------------------------------- : 317
MC-1RC    : HSQELRRTLKEVLTCSCSQDRALVSWDVKSLGGSVCQELLPQQPQEKGLCDQKASSTALQ : 360
MC-1RB    : HSQELRRTLKEVLTCSCSQDRALVSWDVKSLGGSVCQELLPQQPQEKGLCDQKASSTALQ : 360

*       380         *
NM_002386 : --------------------------------------- : -
MC-1RC    : RLLQKEPRGRTSRCSRAPVPSTLDAVLAAEEAGSQPSL : 398
MC-1RB    : RLLQKEVFSLPQAKGPGLQEPP----------------- : 382
```

Fig. 1

MELANOCORTIN-1 RECEPTOR AND METHODS OF USE

DESCRIPTION OF THE DRAWINGS

FIG. 1 shows the amino acid sequence alignments between different forms of the human melanocortin-1 receptor. NM_002386 or MCR-1A (SEQ ID NO 6). MCR-1C (SEQ ID NO 2). MCR-1B (SEQ ID NO 7).

DESCRIPTION OF THE INVENTION

Figure 2:
FIG. 2 shows a schematic of the exon sizes for the melanocortin-1 gene and the tubulin gene (exon 7).

The present invention relates to all facets of novel polynucleotides for melanocortin-1 receptors, the polypeptides they encode, antibodies and specific binding partners thereto, and their applications to research, diagnosis, drug discovery, therapy, clinical medicine, forensic science and medicine, etc. The polynucleotides are useful in variety of ways, including, but not limited to, as molecular markers, as drug targets, and for detecting, diagnosing, staging, monitoring, prognosticating, preventing or treating, determining predisposition to, etc., diseases and conditions especially relating to melanocortin-1, such as melanoma, pigmentation disorders and conditions, inflammation, etc. The identification of a specific genes expressed in pathways physiologically relevant to pigmentation and inflammation permits the definition of functional and disease pathways, and the delineation of targets in these pathways which are useful in diagnostic, therapeutic, and clinical applications. The present invention also relates to methods of using the polynucleotides and related products (proteins, antibodies, etc.) in business and computer-related methods, e.g., advertising, displaying, offering, selling, etc., such products for sale, commercial use, licensing, etc.

The present invention relates to novel forms of a melanocortin-1 receptor (also known as "MCR-1" or alpha-melanocyte stimulating hormone receptor). It is highly expressed in melanocytes, and is a key component of the pathway which modulates skin and hair pigmentation. Moreover, certain alleles of MCR-1 are associated with a high risk of melanoma. MCR-1 is also expressed in other tissues, including monocytes, mast cells, placenta, pituitary, and endothelial cells.

MCR-1 belongs to the G-protein coupled receptor (GPCR) super-family. Its expression is restricted to melanocytes and few other cell types, such as monocytes, mast cells, and endothelial cells. See, e.g., Smith et al., *Gene*, 281:81–94, 2001; Scholzen et al., *Annals of the New York Academy of Sciences*, 885:239–253 (1999). Stimulation of the receptor by its natural ligands (e.g., alpha-melanocyte stimulating hormone or "α-MSH") causes an increase in cAMP levels which, in turn, stimulates intracellular tyrosinase activity. Increased activity of the tyrosinase enzyme drives the conversion of phaeomelanin (yellow and red pigments) to eumelalanin (brown and black pigments).

The MCR-1 gene is located at chromosomal position 16q24. It is adjacent to the tubulin TUBB4 gene, and its 3' region overlaps with the tubulin promoter (Smith et al.). Transcripts containing genic material from both MCR1 and TUBB4 have been identified, including transcripts which contain coding sequences from both. See, e.g., NCBI accession number BC020171. These may be involved in cancer.

Almost 40 different polymorphisms in the MCR receptor have been identified. See, Sturm et al., *Gene*, 277:49–62, 2001; Table 1. Several of these (e.g., Arg151Cys; Arg160Trp; Asp294His) are strongly associated with red hair, fair skin, and poor tanning ability. It has been reported that these alleles are nonfunctional receptors and do not stimulate cAMP production when stimulated by MSH. See, Table 2. As a consequence, phaeomelanin is not converted to eumelalanin, and skin and hair color reflect the cell's high content of the yellow and red phaeomelanin pigments. Significantly, individuals who have these alleles are also at a higher risk for skin cancers, such as basal cell carcinoma, squamous cell carcinoma, and melanoma. See, e.g., Sturm et al., *Am. J. Hum. Genet.*, 6 (supplement to volume 67): 16, Oct. 16, 2000. See, also OMIM, No. 155555 for other information on MCR-1, including disease information, polymorphisms, etc.

The present invention relates to novel forms of MCR-1. In one embodiment, the present invention relates to a novel MCR-1 variant, MCR-1 type C or MCR-1C, which possesses a unique carboxy-terminus. Previous reports had identified a 317 amino acid form of MCR-1 ("MCR-1A") in a number of different species, including human (SEQ ID NO 6), chimpanzee, muskox, sheep, cow, horse, dog, and fox. This form was characterized as full-length. Several minor size variants were observed, as well, e.g., in mouse (315 amino acid acids), in pig (310 amino acids), and in cow (321 amino acids). A second form, MCR-1B, was (SEQ ID NO 7) also reported that had an additional 65 amino acids at its terminus (Tan et al., *FEBS Letters*, 451:137–141, 1991; WO 00/39147). The present invention relates to a third form of MCR-1 (MCR-1C) that comprises 32 carboxy-amino acids (amino acids 367–398 of SEQ ID NO 2) not previously identified in any melanocortin receptor variant. This novel form comprises part of the new carboxy terminus identified in MCR-1B, but diverges from it at amino acid position 367. See, FIG. 1.

FIG. 2 shows exons which have been detected in melanocortin-1 receptors. Exons 1, 2, and 3 contain MCR coding sequences; Exons 5, 6, and 7 contain tubulin coding sequences. MCR-1A (e.g., NM_002386) contains exon 1, and MCR-1B contains exons 1 and 2. MCR-1C contains coding sequence from exons 1–3. As indicated by the stop codon TGA, exon 3 comprises both coding and noncoding sequence. MCR-1C can also contain noncoding sequences, e.g., exons 4, 5, 6, and/or 7 (e.g., for a total of exons 1–7). BC020171, mentioned above, contains the coding sequence from exons 1 and 2 fused to the coding sequences of tubulin in exons 5–7.

The present invention also relates to a polymorphism at amino acid position 120, where an isoleucine (I) is replaced with a threonine (T). Isoleucine is present at amino acid position 120 in most melanocortin receptor-1 homologs, except pig which has a methionine substitution. This polymorphism may affect the receptor's functionality. Analysis of the transmembrane structure using TMHMM v. 2.0 (Krogh et al., *Journal of Molecular Biology*, 305(3):567–580, January 2001; Sonnhammer et al., In J. Glasgow et al., editors, *Proceedings of the Sixth International Conference on Intelligent Systems for Molecular Biology*, pages 175–182, Menlo Park, Calif., 1998. AAAI Press; Moller et al., *Bioinformatics*, 17(7):646–653, July 2001) reveals a different number of predicted transmembrane sequences than the isoleucine isoform.

The present invention relates to any polynucleotide, or polypeptide encoded thereby, which codes for MCR-1C, including receptors having any polymorphism, such as the naturally-occurring polymorphisms listed in Tables 1 and 2, and those disclosed herein. Examples include SEQ ID 3 having 120T and 163Q, SEQ 4 having 120I and 163R, and SEQ ID 5 having 120I and 163Q. It also includes polynucleotide and polypeptide fragments which are specific for MCR-1C (e.g., 367–398 of SEQ ID NO 2 and fragments thereof), and polynucleotides and polypeptides which comprise such specific fragments. For example, the present invention relates to a polynucleotide comprising a coding sequence for amino acid 367–398 of SEQ ID NO 2, or fragments thereof, such as any five amino acid sequence contained therein.

The present invention also relates to an isolated polynucleotide comprising, a polynucleotide sequence coding without interruption for a human MCR-1C, said MCR-1C having about 80%, 85%, 88%, 89%, 90%, 92%, 95%, 99%, etc., or more amino acid sequence identity along its entire length to the amino acid sequence set forth in SEQ ID NO 2, or a complement thereto, and which has ligand-binding activity, G-protein binding activity, or cAMP production activity. For example, such a polynucleotide can comprise one or more of the polymorphisms listed in Tables 1 and 2 (e.g., if 36 of the listed polymorphisms were present in such a polynucleotide, it would have about 90% (360/398) sequence identity along its entire length to the amino acid sequence of SEQ ID NO 2). A corresponding amount of nucleotide is included, e.g., 90%, 92%, 95%, 97%, 98%, 99%, or more.

Similarly, the present invention relates An isolated polynucleotide comprising, a polynucleotide sequence coding without interruption for a human MCR-1C, or complement thereto, said MCR-1C having 80%, 84%, 85%, 86%, 88%, 90%, 95%, or more amino acid sequence identity along its entire length to the sequence comprising amino acids 1–316 of SEQ ID NO 2, and 85%, 90%, 92%, 95%, etc. or more amino acid sequence identity along its entire length to the sequence comprising from amino acids 317–398 of SEQ ID NO 2, and which has ligand-binding activity, G-protein binding activity, or cAMP production activity.

As stated, a polynucleotide can code for a polypeptide having one or more of the following activities, ligand-binding activity, G-protein binding activity, cAMP production activity, or other functional activities. Ligand-binding activity indicates the ability of MCR-1C to bind specifically to a receptor ligand, such as a ACTH, MSH, etc. Ligand binding activity can be using a radioactive or otherwise labeled ligand, or whole-cell assays using labeled ligands. See, e.g., WO0039147, WO9957148, U.S. Pat. Nos. 5,731,408, 6,100,048, and 6,350,760; Libert et al., *Pigment Cell Res.*, 2:510–518, 1989.

G-protein binding activity indicates the ability of the receptor protein to bind to a G-protein. Such binding does not determined routinely, e.g., using filtration assys necessarily have to be productive, i.e., the binding does not have to result in stimulation of the signal transduction cascade. G-protein binding can be measured using in vivo and in vitro binding assays, as well as functional assays. See, e.g., Ford et al., *Science*, 280:1271–1274, 1998.

cAMP production is a measure of the ability of the receptor to stimulate the generation of cAMP upon binding by a receptor agonist. MCR is known to couple to G-proteins and thereby activate adenyl cyclase, increasing intracellular levels of cAMP (e.g., Buckley & Ramachandran, *Proc. Natl. Acad. Sci.*, 78: 7431–7435, 1981; Grahame-Smith et al., 1967, *J. Biol. Chem.* 242: 5535–5541; Mertz & Catt, 1991, *Proc. Natl. Acad. Sci.* 88: 8525–8529; Pawalek et al., 1976, *Invest. Dermatol.* 66: 200–209). This property of cells expressing the MCR-1C can be used assess its "cAMP production activity." For example, cells can be transfected with MCR-1C DNA, plated, and washed once with DMEM containing 1% bovine serum albumin (BSA) and 0.5 mM IBMX (a phosphodiesterase inhibitor). The cells can then be treated with hormone (e.g., alpha-MSH, gamma-MSH, ACTH, etc.). Following hormone treatment, the cells can be washed with phosphate buffered saline, and intracellular cAMP extracted by lysing the cells. Intracellular cAMP concentrations can be determined routinely, e.g., using an assay (Amersham) which measures the ability of cAMP to displace cAMP from a high affinity cAMP binding protein (see Gilman, 1970, *Proc. Natl. Acad. Sci.*, 67: 305–312).

Polynucleotide and polypeptides of the present invention can be used for a variety of purposes, including, but not limited to, treating cancers, treating skin cancer and other cancers modulating skin and hair pigmentation, identifying MCR ligands, modulating the MCR-1 receptor types, determining susceptibility to skin cancer, detecting MCR-1C expression, determining polymorphisms in MCR-1C, making MCR-1C polypeptide, expressing MCR-1C in host cells, making antibodies to MCR-1 receptor types, modulating cutaneous inflammation (see, e.g., Bhardwaj et al., *J. Immunol.*, 158:3378–3384, 1997; Luger et al., *Ann. NY Acad. Sci.*, 917:232–238, 2000), modulating melanocytes, monocytes, endothelial cells, or other cells in which MCR-1C is expressed, etc.

The expression of MCR-1C on the surface of melanoma cells makes it a useful target. Melanoma is a skin cancer which originates from melanocytes present normally in the epidermis and underlying cell layers. There are four basic types: lentigo maligma melanoma, superficial spreading melanoma, nodular melanoma, and acral lentigous melanoma. Because of its expression on melanocytes, MCR-1C specific antibodies and other binding partners can be used to treat melanoma, e.g., by conjugating cytotoxic agents to antibodies directed to the receptor. In addition, MCR-1C polynucleotides, polypeptides, and binding partners thereto can be used to detect metastatic melanoma cells.

Modulation of the MCR-1C can also be used to modulate skin pigmentation, e.g., to increase the amount brown and black pigments to darken skin color, to provide protective effects against UV radiation, to block receptor activation, e.g., preventing or reducing the accumulation of brown and black pigments in the skin, preventing or reducing tanning, preventing or reducing skin freckling, etc. Agonists and antagonists of the melanocortin receptor, include, alpha-melanocyte stimulating hormone and adrenocorticotropic hormone. Other ligands are disclosed in, e.g., WO9957148, U.S. Pat. Nos. 5,731,408, 6,100,048, and 6,350,760, and can be identified and isolated as described in these patents, as well as WO0039147.

As discussed earlier, several MCR-1 alleles have been associated with a greater risk of skin cancer. For example, the presence of the Asp84Glu variant imposed a high risk of melanoma in individual carriers. See, Kennedy et al., *J. Invest. Dermatol.*, 117:294–300, 2001. Other alleles with increased risk of melanoma included, Va160Leu, Va192Met, Arg142His, Arg151Cys, Arg160Trp, Arg163Gln, and His260Pro (Kennedy et al.). See, also, Scott et al., *J. Cell. Sci.*, 115 (Pt. 11):2349–2355, 2002. MCR-1C of the present invention can be used to assess melanoma risks, e.g., determining the presence of a variant of MCR-1C in individuals, and whether such variants are associated with skin cancer and other melanocyte disorders. Analysis can be performed by any suitable method, e.g., by single-stranded conformation polymorphism analysis and DNA sequence analysis.

Expression can also be "selective," where expression is observed. By the phrase "selectively expressed," it is meant that a nucleic acid molecule comprising the defined sequence of nucleotides, when produced as a transcript, is characteristic of the tissue or cell-type in which it is made. This can mean that the transcript is expresseed preferentially, and in no other tissue-type, or it can mean that the transcript is expressed preferentially, differentially, and more abundantly (e.g., at least 5-fold, 10-fold, etc., or more) in that tissue when compared to other tissue-types.

In view of their selectivity and display on the cell surface, MCR-1C polypeptides of the present invention are a useful target for histological, diagnostic, and therapeutic applications relating to the cells in which they are expressed. Antibodies and other protein binding partners (e.g., ligands, aptamers, small peptides, etc.) can be used to selectively target agents to a tissue for any purpose, included, but not limited to, imaging, therapeutic, diagnostic, drug delivery, gene therapy, etc. For example, binding partners, such as antibodies, can be used to treat melanomas in analogy to how c-erbB-2 antibodies are used to breast cancer. They can also be used to detect metastatic cells, in biopsies, etc. The genes and polypeptides encoded thereby can also be used in tissue engineering to identify tissues as they appear during the differentiation process, to target tissues, to modulate tissue growth (e.g., from starting stem cell populations), etc. Useful antibodies or other binding partners include those that are specific for parts of the polypeptide which are exposed extracellularly. Any of the methods described above and below can be accomplished in vivo, in vitro, or ex vivo.

Binding partners can also be used as to specifically deliver therapeutic agents to a tissue of interest. For example, a gene to be delivered to a tissue can be conjugated to a binding partner (directly or through a polymer, etc.), in liposomes comprising cell surface, and then administered as appropriate to the subject who is to be treated. Additionally, cytotoxic, cytostatic, and other therapeutic agents can be delivered specifically to the tissue to treat and/or prevent any of the conditions associated with the tissue of interest.

The present invention relates to methods of detecting melanoma cells, comprising one or more of the following steps, e.g., contacting a sample comprising cells with a polynucleotide specific for MCR-1C (e.g., amino acids 367–398, and fragments thereof), or a mammalian homolog thereof, under conditions effective for said polynucleotide to hybridize specifically to said gene, and detecting specific hybridization. Detecting can be accomplished by any suitable method and technology, including, e.g., any of those mentioned and discussed below, such as Northern blot and PCR. Specific polynucleotides include SEQ ID NOS 8–10, and complements thereto.

As indicated above, binding partners can be used to deliver agents specifically to melanocytes, e.g., for diagnostic, therapeutic, and prognostic purposes, including the treatment of melanoma. Methods of delivering an agent to a melanocyte cell can comprise, e.g., contacting a melanocyte with an agent coupled to binding partner specific for a melanocortin receptor gene of the present invention, whereby said agent is delivered to said cell. Any type of agent can be used, including, therapeutic and imaging agents. Contact with the melanocyte (e.g., a melanoma) can be achieved in any effective manner, including by administering effective amounts of the agent to a host orally, parentally, locally, systemically, intravenously, etc. The phrase "an agent coupled to binding partner" indicates that the agent is associated with the binding partner in such a manner that it can be carried specifically to the target site. Coupling includes, chemical bonding, covalent bonding, noncovalent bonding (where such bonding is sufficient to carry the agent to the target), present in a lipo some or in a lipid membrane, associated with a carrier, such as a polymeric carrier, etc. The agent can be directly linked to the binding partner, or via chemical linkers or spacers.

Imaging of specific organs can be facilitated using tissue selective antibodies and other binding partners that selectively target contrast agents to a specific site in the body. Various imaging techniques have been used in this context, including, e.g., X-ray, CT, CAT, MRI, ultrasound, PET, SPECT, and scintographic. A reporter agent can be conjugated or associated routinely with a binding partner. Ultrasound contrast agents combined with binding partners, such as antibodies, are described in, e.g., U.S. Pat. Nos. 6,264,917, 6,254,852, 6,245,318, and 6,139,819. MRI contrast agents, such as metal chelators, radionucleotides, paramagnetic ions, etc., combined with selective targeting agents are also described in the literature, e.g., in U.S. Pat. Nos. 6,280,706 and 6,221,334. The methods described therein can be used generally to associate a partner with an agent for any desired purpose.

Nucleic Acids

A mammalian polynucleotide, or fragment thereof, of the present invention is a polynucleotide having a nucleotide sequence obtainable from a natural source. When the species name is used, it indicates that the polynucleotide or polypeptide is obtainable from a natural source. It therefore includes naturally-occurring normal, naturally-occurring mutant, and naturally-occurring polymorphic alleles (e.g., SNPs), differentially-spliced transcripts, splice-variants, etc. By the term "naturally-occurring," it is meant that the polynucleotide is obtainable from a natural source, e.g., animal tissue and cells, body fluids, tissue culture cells, forensic samples. Natural sources include, e.g., living cells obtained from tissues and whole organisms, tumors, cultured cell lines, including primary and immortalized cell lines. Naturally-occurring mutations can include deletions (e.g., a truncated amino- or carboxy-terminus), substitutions, inversions, or additions of nucleotide sequence. These genes can be detected and isolated by polynucleotide hybridization according to methods which one skilled in the art would know, e.g., as discussed below.

A polynucleotide according to the present invention can be obtained from a variety of different sources. It can be obtained from DNA or RNA, such as polyadenylated mRNA or total RNA, e.g., isolated from tissues, cells, or whole organism. The polynucleotide can be obtained directly from DNA or RNA, from a cDNA library, from a genomic library, etc. The polynucleotide can be obtained from a cell or tissue (e.g., from an embryonic or adult tissues) at a particular stage of development, having a desired genotype, phenotype, disease status, etc. A polynucleotide which "codes without interruption" refers to a polynucleotide having a continuous open reading frame ("ORF") as compared to an ORF which is interrupted by introns or other noncoding sequences, e.g., a cDNA.

Polynucleotides and polypeptides can be excluded as compositions from the present invention if, e.g., listed in a publicly available databases on the day this application was filed and/or disclosed in a patent application having an earlier filing or priority date than this application and/or conceived and/or reduced to practice earlier than a polynucleotide in this application, or the expression pattern thereof.

As described herein, the phrase "an isolated polynucleotide which is SEQ ID NO," or "an isolated polynucleotide which is selected from SEQ ID NO," refers to an isolated nucleic acid molecule from which the recited sequence was derived (e.g., a cDNA derived from mRNA; cDNA derived from genomic DNA). Because of sequencing errors, typographical errors, etc., the actual naturally-occurring sequence may differ from a SEQ ID listed herein. Thus, the phrase indicates the specific molecule from which the sequence was derived, rather than a molecule having that exact recited nucleotide sequence, analogously to how a culture depository number refers to a specific cloned fragment in a cryotube.

As explained in more detail below, a polynucleotide sequence of the invention can contain a complete coding sequence, degenerate sequences thereof, anti-sense, muteins thereof, genes comprising said sequences, full-length cDNAs comprising said sequences, complete genomic sequences, fragments thereof, homologs, primers, nucleic acid molecules which hybridize thereto, derivatives thereof, etc.

Genomic

The present invention also relates genomic DNA from which the polynucleotides of the present invention can be derived. A genomic DNA coding for a human, mouse, or other mammalian polynucleotide, can be obtained routinely, for example, by screening a genomic library (e.g., a YAC library) with a polynucleotide of the present invention, or by searching nucleotide databases, such as GenBank and EMBL, for matches. Promoter and other regulatory regions (including both 5' and 3' regions, as well introns) can be identified upstream or downstream of coding and expressed RNAs, and assayed routinely for activity, e.g., by joining to a reporter gene (e.g., CAT, GFP, alkaline phosphatase, luciferase, galatosidase). A promoter obtained from a melanocortin-1C receptor can be used, e.g., in gene therapy to obtain tissue-specific expression of a heterologous gene (e.g., coding for a therapeutic product or cytotoxin). 5' and 3' sequences (including, UTRs and introns) can be used to modulate or regulate stability, transcription, and translation of nucleic acids, including the sequence to which is attached in nature, as well as heterologous nucleic acids. Examples of promoters for MCR-1C include, e.g., SEQ ID NOS 11–13.

Constructs

A polynucleotide of the present invention can comprise additional polynucleotide sequences, e.g., sequences to enhance expression, detection, uptake, cataloging, tagging, etc. A polynucleotide can include only coding sequence; a coding sequence and additional non-naturally occurring or heterologous coding sequence (e.g., sequences coding for leader, signal, secretory, targeting, enzymatic, fluorescent, antibiotic resistance, and other functional or diagnostic peptides); coding sequences and non-coding sequences, e.g., untranslated sequences at either a 5' or 3' end, or dispersed in the coding sequence, e.g., introns.

A polynucleotide according to the present invention also can comprise an expression control sequence operably linked to a polynucleotide as described above. The phrase "expression control sequence" means a polynucleotide sequence that regulates expression of a polypeptide coded for by a polynucleotide to which it is functionally ("operably") linked. Expression can be regulated at the level of the mRNA or polypeptide. Thus, the expression control sequence includes mRNA-related elements and protein-related elements. Such elements include promoters, enhancers (viral or cellular), ribosome binding sequences, transcriptional terminators, etc. An expression control sequence is operably linked to a nucleotide coding sequence when the expression control sequence is positioned in such a manner to effect or achieve expression of the coding sequence. For example, when a promoter is operably linked 5' to a coding sequence, expression of the coding sequence is driven by the promoter. Expression control sequences can include an initiation codon and additional nucleotides to place a partial nucleotide sequence of the present invention in-frame in order to produce a polypeptide (e.g., pET vectors from Promega have been designed to permit a molecule to be inserted into all three reading frames to identify the one that results in polypeptide expression). Expression control sequences can be heterologous or endogenous to the normal gene.

A polynucleotide of the present invention can also comprise nucleic acid vector sequences, e.g., for cloning, expression, amplification, selection, etc. Any effective vector can be used. A vector is, e.g., a polynucleotide molecule which can replicate autonomously in a host cell, e.g., containing an origin of replication. Vectors can be useful to perform manipulations, to propagate, and/or obtain large quantities of the recombinant molecule in a desired host. A skilled worker can select a vector depending on the purpose desired, e.g., to propagate the recombinant molecule in bacteria, yeast, insect, or mammalian cells. The following vectors are provided by way of example. Bacterial: pQE70, pQE60, pQE-9 (Qiagen), pBS, pD10, Phagescript, phiX174, pBK Phagemid, pNH8A, pNH16a, pNH18Z, pNH46A (Stratagene); Bluescript KS+II (Stratagene); ptrc99a, pKK223-3, pKK233-3, pDR540, pRIT5 (Pharmacia). Eukaryotic: PWLNEO, pSV2CAT, pOG44, pXT1, pSG (Stratagene), pSVK3, PBPV, PMSG, pSVL (Pharmacia), pCR2.1/TOPO, pCRII/TOPO, pCR4/TOPO, pTrcHisB, pCMV6-XL4, etc. However, any other vector, e.g., plasmids, viruses, or parts thereof, may be used as long as they are replicable and viable in the desired host. The vector can also comprise sequences which enable it to replicate in the host whose genome is to be modified.

Hybridization

Polynucleotide hybridization, as discussed in more detail below, is useful in a variety of applications, including, in gene detection methods, for identifying mutations, for making mutations, to identify homologs in the same and different species, to identify related members of the same gene family, in diagnostic and prognostic assays, in therapeutic applications (e.g., where an antisense polynucleotide is used to inhibit expression), etc.

The ability of two single-stranded polynucleotide preparations to hybridize together is a measure of their nucleotide sequence complementarity, e.g., base-pairing between nucleotides, such as A-T, G-C, etc. The invention thus also relates to polynucleotides, and their complements, which hybridize to a polynucleotide comprising a nucleotide sequence as set forth in SEQ ID NO 1 and genomic sequences thereof. A nucleotide sequence hybridizing to the latter sequence will have a complementary polynucleotide strand, or act as a template for one in the presence of a polymerase (i.e., an appropriate polynucleotide synthesizing enzyme). The present invention includes both strands of polynucleotide, e.g., a sense strand and an anti-sense strand.

Hybridization conditions can be chosen to select polynucleotides which have a desired amount of nucleotide complementarity with a nucleotide sequence as set forth in SEQ ID NO 1 and genomic sequences thereof. A polynucleotide capable of hybridizing to such sequence, preferably, possesses, e.g., about 70%, 75%, 80%, 85%, 87%, 90%, 92%, 95%, 97%, 99%, or 100% complementarity, between the sequences. The present invention particularly relates to polynucleotide sequences which hybridize to a nucleotide sequence as set forth in SEQ ID NO 1 or genomic sequences thereof, under low or high stringency conditions. These conditions can be used, e.g., to select corresponding homologs in non-human species.

Polynucleotides which hybridize to polynucleotides of the present invention can be selected in various ways. Filter-type blots (i.e., matrices containing polynucleotide, such as nitrocellulose), glass chips, and other matrices and substrates comprising polynucleotides (short or long) of interest, can be incubated in a prehybridization solution (e.g., 6× SSC, 0.5% SDS, 100 μg/ml denatured salmon sperm DNA, 5× Denhardt's solution, and 50% formamide), at 22–68° C., overnight, and then hybridized with a detectable polynucleotide probe under conditions appropriate to achieve the desired stringency. In general, when high homology or sequence identity is desired, a high temperature can be used (e.g., 65° C.). As the homology drops, lower washing temperatures are used. For salt concentrations, the lower the salt concentration, the higher the stringency. The length of the probe is another consideration. Very short probes (e.g., less than 100 base pairs) are washed at lower temperatures, even if the homology is high. With short probes, formamide can be omitted. See, e.g., *Current Protocols in Molecular Biology*, Chapter 6, Screening of Recombinant Libraries; Sambrook et al., *Molecular Cloning*, 1989, Chapter 9.

For instance, high stringency conditions can be achieved by incubating the blot overnight (e.g., at least 12 hours) with a long polynucleotide probe in a hybridization solution containing, e.g., about 5× SSC, 0.5% SDS, 100 μg/ml denatured salmon sperm DNA and 50% formamide, at 42° C. Blots can be washed at high stringency conditions that allow, e.g., for less than 5% bp mismatch (e.g., wash twice in 0.1% SSC and 0.1% SDS for 30 min at 65° C.), i.e., selecting sequences having 95% or greater sequence identity.

Other non-limiting examples of high stringency conditions includes a final wash at 65° C. in aqueous buffer containing 30 mM NaCl and 0.5% SDS. Another example of high stringent conditions is hybridization in 7% SDS, 0.5 M NaPO$_4$, pH 7, 1 mM EDTA at 50° C., e.g., overnight, followed by one or more washes with a 1% SDS solution at 42° C. Whereas high stringency washes can allow for less than 5% mismatch, reduced or low stringency conditions can permit up to 20% nucleotide mismatch. Hybridization at low stringency can be accomplished as above, but using lower formamide conditions, lower temperatures and/or lower salt concentrations, as well as longer periods of incubation time.

Hybridization can also be based on a calculation of melting temperature (Tm) of the hybrid formed between the probe and its target, as described in Sambrook et al.. Generally, the temperature Tm at which a short oligonucleotide (containing 18 nucleotides or fewer) will melt from its target sequence is given by the following equation: Tm=(number of A's and T's)×2° C.+(number of C's and G's)×4° C. For longer molecules, Tm=81.5+16.6 log$_{10}$[Na$^+$]+0.41 (%GC)−600/N where [Na$^+$] is the molar concentration of sodium ions, % GC is the percentage of GC base pairs in the probe, and N is the length. Hybridization can be carried out at several degrees below this temperature to ensure that the probe and target can hybridize. Mismatches can be allowed for by lowering the temperature even further.

Stringent conditions can be selected to isolate sequences, and their complements, which have, e.g., at least about 80%, 85%, 90%, 95%, 97%, or 99% nucleotide complementarity between the probe (e.g., a short polynucleotide of SEQ ID NO 1 or genomic sequences thereof) and a target polynucleotide.

Other homologs of polynucleotides of the present invention can be obtained from mammalian and non-mammalian sources according to various methods. For example, hybridization with a polynucleotide can be employed to select homologs, e.g., as described in Sambrook et al., *Molecular Cloning*, Chapter 11, 1989. Such homologs can have varying amounts of nucleotide and amino acid sequence identity and similarity to such polynucleotides of the present invention. Mammalian organisms include, e.g., mice, rats, monkeys, pigs, cows, etc. Non-mammalian organisms include, e.g., vertebrates, invertebrates, zebra fish, chicken, Drosophila, *C. elegans*, Xenopus, yeast such as *S. pombe, S. cerevisiae*, roundworms, prokaryotes, plants, Arabidopsis, artemia, viruses, etc. The degree of nucleotide sequence identity between human and mouse can be about, e.g. 70% or more, 85% or more, 90% or more, 95% or more, etc., for open reading frames.

Alignment

Alignments can be accomplished by using any effective algorithm. For pairwise alignments of DNA sequences, the methods described by Wilbur-Lipman (e.g., Wilbur and Lipman, *Proc. Natl. Acad. Sci.*, 80:726–730, 1983) or Martinez/Needleman-Wunsch (e.g., Martinez, *Nucleic Acid Res.*, 11:4629–4634, 1983) can be used. For instance, if the Martinez/Needleman-Wunsch DNA alignment is applied, the minimum match can be set at 9, gap penalty at 1.10, and gap length penalty at 0.33. The results can be calculated as a similarity index, equal to the sum of the matching residues divided by the sum of all residues and gap characters, and then multiplied by 100 to express as a percent. Similarity index for related genes at the nucleotide level in accordance with the present invention can be greater than 70%, 80%, 85%, 90%, 95%, 99%, or more. Pairs of protein sequences can be aligned by the Lipman-Pearson method (e.g., Lipman and Pearson, *Science,* 227:1435–1441, 1985) with k-tuple set at 2, gap penalty set at 4, and gap length penalty set at 12. Results can be expressed as percent similarity index, where related genes at the amino acid level in accordance with the present invention can be greater than 65%, 70%, 75%, 80%, 85%, 90%, 95%, 99%, or more. Various commercial and free sources of alignment programs are available, e.g., MegAlign by DNA Star, BLAST (National Center for Biotechnology Information), BCM (Baylor College of Medicine) Launcher, etc. BLAST can be used to calculate amino acid sequence identity, amino acid sequence homology, and nucleotide sequence identity. These calculations can be made along the entire length of each of the target sequences which are to be compared.

After two sequences have been aligned, a "percent sequence identity" can be determined. For these purposes, it is convenient to refer to a Reference Sequence and a Compared Sequence, where the Compared Sequence is compared to the Reference Sequence. Percent sequence identity can be determined according to the following formula: Percent Identity=100[1−(C/R)], wherein C is the number of differences between the Reference Sequence and the Compared Sequence over the length of alignment between the Reference Sequence and the Compared Sequence where (i) each base or amino acid in the Reference Sequence that does not have a corresponding aligned base or amino acid in the Compared Sequence, (ii) each gap in the Reference Sequence, (iii) each aligned base or amino acid in the Reference Sequence that is different from an aligned base or amino acid in the Compared Sequence, constitutes a difference; and R is the number of bases or amino acids in the Reference Sequence over the length of the alignment with the Compared Sequence with any gap created in the Reference Sequence also being counted as a base or amino acid.

Percent sequence identity can also be determined by other conventional methods, e.g., as described in Altschul et al., Bull. Math. Bio. 48: 603–616, 1986 and Henikoff and Henikoff, Proc. Natl. Acad. Sci. USA 89:10915–10919, 1992.

Specific Polynucleotide Probes

A polynucleotide of the present invention can comprise any continuous nucleotide sequence of SEQ ID NO 1, sequences which share sequence identity thereto, or complements thereof. The term "probe" refers to any substance that can be used to detect, identify, isolate, etc., another substance. A polynucleotide probe is comprised of nucleic acid can be used to detect, identify, etc., other nucleic acids, such as DNA and RNA. Examples of probes include, SEQ ID NOS 1–3.

These polynucleotides can be of any desired size that is effective to achieve the specificity desired. For example, a probe can be from about 7 or 8 nucleotides to several thousand nucleotides, depending upon its use and purpose. For instance, a probe used as a primer PCR can be shorter than a probe used in an ordered array of polynucleotide probes. Probe sizes vary, and the invention is not limited in any way by their size, e.g., probes can be from about 7–2000 nucleotides, 7–1000, 8–700, 8–600, 8–500, 8–400, 8–300, 8–150, 8–100 8–75, 7–50, 10–25, 14–16, at least about 8, at least about 10, at least about 15, at least about 25, etc. The polynucleotides can have non-naturally-occurring nucleotides, e.g., inosine, AZT, 3TC, etc. The polynucleotides can have 100% sequence identity or complementarity to a sequence set forth in SEQ ID NO 1, or it can have mismatches or nucleotide substitutions, e.g., 1, 2, 3, 4, or 5 substitutions. The probes can be single-stranded or double-stranded.

In accordance with the present invention, a polynucleotide can be present in a kit, where the kit includes, e.g., one or more polynucleotides, a desired buffer (e.g., phosphate, tris, etc.), detection compositions, RNA or cDNA from different tissues to be used as controls, libraries, etc. The polynucleotide can be labeled or unlabeled, with radioactive or non-radioactive labels as known in the art. Kits can comprise one or more pairs of polynucleotides for amplifying nucleic acids specific for a melanocortin receptor gene of the present invention, e.g., comprising a forward and reverse primer effective in PCR. These include both sense and anti-sense orientations. For instance, in PCR-based methods (such as RT-PCR), a pair of primers are typically used, one having a sense sequence and the other having an antisense sequence.

Another aspect of the present invention is a nucleotide sequence that is specific to, or for, a selective polynucleotide. The phrases "specific for" or "specific to" a polynucleotide have a functional meaning that the polynucleotide can be used to identify the presence of one or more target genes in a sample and distinguish them from non-target genes. It is specific in the sense that it can be used to detect polynucleotides above background noise ("non-specific binding"). A specific sequence is a defined order of nucleotides (or amino acid sequences, if it is a polypeptide sequence) which occurs in the polynucleotide, e.g., in the nucleotide sequence set forth in SEQ ID NO 1, and which is characteristic of that target sequence, and substantially no non-target sequences. A probe or mixture of probes can comprise a sequence or sequences that are specific to a plurality of target sequences, e.g., where the sequence is a consensus sequence, a functional domain, etc., e.g., capable of recognizing a family of related genes. Such sequences can be used as probes in any of the methods described herein or incorporated by reference. Both sense and antisense nucleotide sequences are included. A specific polynucleotide according to the present invention can be determined routinely.

A polynucleotide comprising a specific sequence can be used as a hybridization probe to identify the presence of, e.g., human or mouse polynucleotide, in a sample comprising a mixture of polynucleotides, e.g., on a Northern blot. Hybridization can be performed under high stringent conditions (see, above) to select polynucleotides (and their complements which can contain the coding sequence) having at least 90%, 95%, 99%, etc., identity (i.e., complementarity) to the probe, but less stringent conditions can also be used. A specific polynucleotide sequence can also be fused in-frame, at either its 5' or 3' end, to various nucleotide sequences as mentioned throughout the patent, including coding sequences for enzymes, detectable markers, GFP, etc, expression control sequences, etc.

A polynucleotide probe, especially one that is specific to a polynucleotide of the present invention, can be used in gene detection and hybridization methods as already described. In one embodiment, a specific polynucleotide probe can be used to detect whether a particular tissue or cell-type is present in a target sample. To carry out such a method, a selective polynucleotide can be chosen which is characteristic of the desired target tissue. Such polynucleotide is preferably chosen so that it is expressed or displayed in the target tissue, but not in other tissues which are present in the sample. For instance, if detection of melanocytes or a melanoma is desired, it may not matter whether the selective polynucleotide is expressed in other tissues. Starting from the selective polynucleotide, a specific polynucleotide probe can be designed which hybridizes (if hybridization is the basis of the assay) under the hybridization conditions to the selective polynucleotide, whereby the presence of the selective polynucleotide can be determined.

Probes which are specific for polynucleotides of the present invention can also be prepared using involve transcription-based systems, e.g., incorporating an RNA polymerase promoter into a selective polynucleotide of the present invention, and then transcribing anti-sense RNA using the polynucleotide as a template. See, e.g., U.S. Pat. No. 5,545,522.

Polynucleotide Composition

A polynucleotide according to the present invention can comprise, e.g., DNA, RNA, synthetic polynucleotide, peptide polynucleotide, modified nucleotides, dsDNA, ssDNA, ssRNA, dsRNA, and mixtures thereof. A polynucleotide can be single- or double-stranded, triplex, DNA:RNA, duplexes, comprise hairpins, and other secondary structures, etc. Nucleotides comprising a polynucleotide can be joined via various known linkages, e.g., ester, sulfamate, sulfamide, phosphorothioate, phosphoramidate, methylphosphonate, carbamate, etc., depending on the desired purpose, e.g., resistance to nucleases, such as RNAse H, improved in vivo stability, etc. See, e.g., U.S. Pat. No. 5,378,825. Any desired nucleotide or nucleotide analog can be incorporated, e.g., 6-mercaptoguanine, 8-oxo-guanine, etc.

Various modifications can be made to the polynucleotides, such as attaching detectable markers (avidin, biotin, radioactive elements, fluorescent tags and dyes, energy transfer labels, energy-emitting labels, binding partners, etc.) or moieties which improve hybridization, detection, and/or stability. The polynucleotides can also be attached to solid supports, e.g., nitrocellulose, magnetic or paramagnetic microspheres (e.g., as described in U.S. Pat. No. 5,411,863; U.S. Pat. No. 5,543,289; for instance, comprising ferromagnetic, supermagnetic, paramagnetic, superparamagnetic, iron oxide and polysaccharide), nylon, agarose, diazotized cellulose, latex solid microspheres, polyacrylamides, etc., according to a desired method. See, e.g., U.S. Pat. Nos. 5,470,967, 5,476,925, and 5,478,893.

Polynucleotide according to the present invention can be labeled according to any desired method. The polynucleotide can be labeled using radioactive tracers such as $^{32}P$, $^{35}S$, $^{3}H$, or $^{14}C$, to mention some commonly used tracers. The radioactive labeling can be carried out according to any method, such as, for example, terminal labeling at the 3' or 5' end using a radiolabeled nucleotide, polynucleotide kinase (with or without dephosphorylation with a phosphatase) or a ligase (depending on the end to be labeled). A non-radioactive labeling can also be used, combining a polynucleotide of the present invention with residues having immunological properties (antigens, haptens), a specific affinity for certain reagents (ligands), properties enabling detectable enzyme reactions to be completed (enzymes or coenzymes, enzyme substrates, or other substances involved in an enzymatic reaction), or characteristic physical properties, such as fluorescence or the emission or absorption of light at a desired wavelength, etc.

Nucleic Acid Detection Methods

Another aspect of the present invention relates to methods and processes for detecting a melanocortin receptor gene of the present invention. Detection methods have a variety of applications, including for diagnostic, prognostic, forensic, and research applications. To accomplish gene detection, a polynucleotide in accordance with the present invention can be used as a "probe." The term "probe" or "polynucleotide probe" has its customary meaning in the art, e.g., a polynucleotide which is effective to identify (e.g., by hybridization), when used in an appropriate process, the presence of a target polynucleotide to which it is designed. Identification can involve simply determining presence or absence, or it can be quantitative, e.g., in assessing amounts of a gene or gene transcript present in a sample. Probes can be useful in a variety of ways, such as for diagnostic purposes, to identify homologs, and to detect, quantitate, or isolate a polynucleotide of the present invention in a test sample.

Assays can be utilized which permit quantification and/or presence/absence detection of a target nucleic acid in a sample. Assays can be performed at the single-cell level, or in a sample comprising many cells, where the assay is "averaging" expression over the entire collection of cells and tissue present in the sample. Any suitable assay format can be used, including, but not limited to, e.g., Southern blot analysis, Northern blot analysis, polymerase chain reaction ("PCR") (e.g., Saiki et al., *Science*, 241:53, 1988; U.S. Pat. Nos. 4,683,195, 4,683,202, and 6,040,166; PCR Protocols: *A Guide to Methods and Applications*, Innis et al., eds., Academic Press, New York, 1990), reverse transcriptase polymerase chain reaction ("RT-PCR"), anchored PCR, rapid amplification of cDNA ends ("RACE") (e.g., Schaefer in *Gene Cloning and Analysis :Current Innovations*, Pages 99–115, 1997), ligase chain reaction ("LCR") (EP 320 308), one-sided PCR (Ohara et al., *Proc. Natl. Acad. Sci.*, 86:5673–5677, 1989), indexing methods (e.g., U.S. Pat. No. 5,508,169), in situ hybridization, differential display (e.g., Liang et al., *Nucl. Acid. Res.*, 21:3269–3275, 1993; U.S. Pat. Nos. 5,262,311, 5,599,672 and 5,965,409; WO97/18454; Prashar and Weissman, *Proc. Natl. Acad. Sci.*, 93:659–663, and U.S. Pat. Nos. 6,010,850 and 5,712,126; Welsh et al., *Nucleic Acid Res.*, 20:4965–4970, 1992, and U.S. Pat. No. 5,487,985) and other RNA fingerprinting techniques, nucleic acid sequence based amplification ("NASBA") and other transcription based amplification systems (e.g., U.S. Pat. Nos. 5,409,818 and 5,554,527; WO 88/10315), polynucleotide arrays (e.g., U.S. Pat. Nos. 5,143,854, 5,424,186; 5,700,637, 5,874,219, and 6,054,270; PCT WO 92/10092; PCT WO 90/15070), Qbeta Replicase (PCT/US87/00880), Strand Displacement Amplification ("SDA"), Repair Chain Reaction ("RCR"), nuclease protection assays, subtraction-based methods, Rapid-Scan™, etc. Additional useful methods include, but are not limited to, e.g., template-based amplification methods, competitive PCR (e.g., U.S. Pat. No. 5,747,251), redox-based assays (e.g., U.S. Pat. No. 5,871, 918), Taqman-based assays (e.g., Holland et al., *Proc. Natl. Acad, Sci.*, 88:7276–7280, 1991; U.S. Pat. Nos. 5,210,015 and 5,994,063), real-time fluorescence-based monitoring (e.g., U.S. Pat. No. 5,928,907), molecular energy transfer labels (e.g., U.S. Pat. Nos. 5,348,853, 5,532,129, 5,565,322, 6,030,787, and 6,117,635; Tyagi and Kramer, *Nature Biotech.*, 14:303–309, 1996). Any method suitable for single cell analysis of gene or protein expression can be used, including in situ hybridization, immunocytochemistry, MACS, FACS, flow cytometry, etc. For single cell assays, expression products can be measured using antibodies, PCR, or other types of nucleic acid amplification (e.g., Brady et al., *Methods Mol. & Cell. Biol.* 2, 17–25, 1990; Eberwine et al., 1992, *Proc. Natl. Acad. Sci.*, 89, 3010–3014, 1992; U.S. Pat. No. 5,723,290). These and other methods can be carried out conventionally, e.g., as described in the mentioned publications.

Many of such methods may require that the polynucleotide is labeled, or comprises a particular nucleotide type useful for detection. The present invention includes such modified polynucleotides that are necessary to carry out such methods. Thus, polynucleotides can be DNA, RNA, DNA:RNA hybrids, PNA, etc., and can comprise any modification or substituent which is effective to achieve detection.

Detection can be desirable for a variety of different purposes, including research, diagnostic, prognostic, and forensic. For diagnostic purposes, it may be desirable to identify the presence or quantity of a polynucleotide sequence in a sample, where the sample is obtained from tissue, cells, body fluids, etc. In a preferred method as described in more detail below, the present invention relates to a method of detecting a polynucleotide comprising, contacting a target polynucleotide in a test sample with a polynucleotide probe under conditions effective to achieve hybridization between the target and probe; and detecting hybridization.

Any test sample in which it is desired to identify a polynucleotide or polypeptide thereof can be used, including, e.g., blood, urine, saliva, stool (for extracting nucleic acid, see, e.g., U.S. Pat. No. 6,177,251), swabs comprising tissue, biopsied tissue, tissue sections, cultured cells, etc.

Polynucleotides can be used in wide range of methods and compositions, including for detecting, diagnosing, staging, grading, assessing, prognosticating, etc. diseases and disorders of the immune system, for monitoring or assessing therapeutic and/or preventative measures, in ordered arrays, etc. Any method of detecting melanocortin-1 receptor genes and polynucleotides can be used. The present invention is not to be limited how such methods are implemented.

Along these lines, the present invention relates to methods of detecting a melanocortin receptor gene of the present invention in a sample comprising nucleic acid. Such methods can comprise one or more the following steps in any effective order, e.g., contacting said sample with a polynucleotide probe under conditions effective for said probe to hybridize specifically to nucleic acid in said sample, and detecting the presence or absence of probe hybridized to nucleic acid in said sample. The probe can be a polynucleotide sequence selected from SEQ ID NO 1. or a complement thereto, a polynucleotide having, e.g., about 70%, 80%, 85%, 90%, 95%, 99%, or more sequence identity thereto, effective or specific fragments thereof, or complements thereto. The detection method can be applied to any sample, e.g., cultured primary, secondary, or established cell lines, tissue biopsy, blood, urine, stool, cerebral spinal fluid, and other bodily fluids, for any purpose.

Contacting the sample with probe can be carried out by any effective means in any effective environment. It can be accomplished in a solid, liquid, frozen, gaseous, amorphous, solidified, coagulated, colloid, etc., mixtures thereof, matrix. For instance, a probe in an aqueous medium can be contacted with a sample which is also in an aqueous medium, or which is affixed to a solid matrix, or vice-versa.

Generally, as used throughout the specification, the term "effective conditions" means, e.g., the particular milieu in which the desired effect is achieved. Such a milieu, includes, e.g., appropriate buffers, oxidizing agents, reducing agents, pH, co-factors, temperature, ion concentrations, suitable age and/or stage of cell (such as, in particular part of the cell cycle, or at a particular stage where particular genes are being expressed) where cells are being used, culture conditions (including substrate, oxygen, carbon dioxide, etc.). When hybridization is the chosen means of achieving detection, the probe and sample can be combined such that the resulting conditions are functional for said probe to hybridize specifically to nucleic acid in said sample.

The phrase "hybridize specifically" indicates that the hybridization between single-stranded polynucleotides is based on nucleotide sequence complementarity. The effective conditions are selected such that the probe hybridizes to a preselected and/or definite target nucleic acid in the sample. For instance, if detection of MCR-1C is desired, a probe can be selected which can hybridize to such target gene under high stringent conditions, without significant hybridization to other genes in the sample. To detect MCR-1C homologs, the effective hybridization conditions can be less stringent, and/or the probe can comprise codon degeneracy, such that a homolog is detected in the sample.

As already mentioned, the methods can be carried out by any effective process, e.g., by Northern blot analysis, polymerase chain reaction (PCR), reverse transcriptase PCR, RACE PCR, in situ hybridization, etc., as indicated above. When PCR based techniques are used, two or more probes are generally used. One probe can be specific for a defined sequence which is characteristic of a selective polynucleotide, but the other probe can be specific for the selective polynucleotide, or specific for a more general sequence, e.g., a sequence such as polyA which is characteristic of mRNA, a sequence which is specific for a promoter, ribosome binding site, or other transcriptional features, a consensus sequence (e.g., representing a functional domain). For the former aspects, 5' and 3' probes (e.g., polyA, Kozak, etc.) are preferred which are capable of specifically hybridizing to the ends of transcripts. When PCR is utilized, the probes can also be referred to as "primers" in that they can prime a DNA polymerase reaction.

In addition to testing for the presence or absence of polynucleotides, the present invention also relates to determining the amounts at which polynucleotides of the present invention are expressed in sample and determining the differential expression of such polynucleotides in samples. Such methods can involve substantially the same steps as described above for presence/absence detection, e.g., contacting with probe, hybridizing, and detecting hybridized probe, but using more quantitative methods and/or comparisons to standards.

The amount of hybridization between the probe and target can be determined by any suitable methods, e.g., PCR, RT-PCR, RACE PCR, Northern blot, polynucleotide microarrays, Rapid-Scan, etc., and includes both quantitative and qualitative measurements. For further details, see the hybridization methods described above and below. Determining by such hybridization whether the target is differentially expressed (e.g., up-regulated or down-regulated) in the sample can also be accomplished by any effective means. For instance, the target's expression pattern in the sample can be compared to its pattern in a known standard, such as in a normal tissue, or it can be compared to another gene in the same sample. When a second sample is utilized for the comparison, it can be a sample of normal tissue that is known not to contain diseased cells. The comparison can be performed on samples which contain the same amount of RNA (such as polyadenylated RNA or total RNA), or, on RNA extracted from the same amounts of starting tissue. Such a second sample can also be referred to as a control or standard. Hybridization can also be compared to a second target in the same tissue sample. Experiments can be performed that determine a ratio between the target nucleic acid and a second nucleic acid (a standard or control), e.g., in a normal tissue. When the ratio between the target and control are substantially the same in a normal and sample, the sample is determined or diagnosed not to contain cells. However, if the ratio is different between the normal and sample tissues, the sample is determined to contain cancer cells. The approaches can be combined, and one or more second samples, or second targets can be used. Any second target nucleic acid can be used as a comparison, including "housekeeping" genes, such as beta-actin, alcohol dehydrogenase, or any other gene whose expression does not vary depending upon the disease status of the cell.

As mentioned, PCR based methods can also be used in the methods of detecting a gene coding for a human MCR-1C. In such methods, more than one probe specific for the gene can be used, e.g., a pair of specific polynucleotide probes which are capable of amplifying a polynucleotide sequence of MCR-1C, such as corresponding to amino acids 1–366, 367–398, etc., of SEQ ID NO 2. For instance, SEQ ID NO 8 is in exon 1, SEQ ID NO 9 spans exons 2–3, and SEQ ID NO 10 is in exon 4. Thus, in a PCR reaction, SEQ IDS 8 and 9 produce a fragment about 262 base pairs that is absent in MCR-1A and MCR-1B. SEQ ID NOS 8 and 10 in a PCR reaction produce a fragment of about 615 base pairs which is absent from MCR-1A and MCR-1B.

Methods of Identifying Polymorphisms, Mutations, etc.

Polynucleotides of the present invention can also be utilized to identify mutant alleles, SNPs, gene rearrangements and modifications, and other polymorphisms of the wild-type gene. Mutant alleles, polymorphisms, SNPs, etc., can be identified and isolated from melanomas and other skin conditions that are known, or suspected to have, a genetic component. Identification of such genes can be carried out routinely (see, above for more guidance), e.g., using PCR, hybridization techniques, direct sequencing, mismatch reactions (see, e.g., above), RFLP analysis, SSCP (e.g., Orita et al., *Proc. Natl. Acad. Sci.*, 86:2766, 1992), etc., where a polynucleotide having a sequence selected from SEQ ID NO 1 (especially corresponding to amino acids 367–398) can be used as a probe. The selected mutant alleles, SNPs, polymorphisms, etc., can be used diagnostically to determine whether a subject has, or is susceptible to a melanoma or other condition (e.g., pigmentation variation, inflammatory condition) associated with a melanocortin receptor gene of the present invention, as well as to design therapies and predict the outcome of the disorder. Methods involve, e.g., diagnosing a disorder or determining susceptibility to a disorder, comprising, detecting the presence of a mutation in a melanocortin receptor gene of the present invention. The detecting can be carried out by any effective method, e.g., obtaining cells from a subject, determining the gene sequence or structure of a target gene (using, e.g., mRNA, cDNA, genomic DNA, etc), comparing the sequence or structure of the target gene to the structure of the normal gene, whereby a difference in sequence or structure indicates a mutation in the gene in the subject. Polynucleotides can also be used to test for mutations, SNPs, polymorphisms, etc., e.g., using mismatch DNA repair technology as described in U.S. Pat. No. 5,683,877; U.S. Pat. No. 5,656,430; Wu et al., *Proc. Natl. Acad. Sci.*, 89:8779–8783, 1992.

The present invention also relates to methods of detecting polymorphisms in said gene, comprising, e.g., comparing the structure of: genomic DNA comprising all or part of said gene, mRNA comprising all or part of said gene, cDNA comprising all or part of said gene, or a polypeptide comprising all or part of said gene, with the structure of the polyncleotide or amino acid sequence of said gene. The methods can be carried out on a sample from any source, e.g., cells, tissues, body fluids, blood, urine, stool, hair, egg, sperm, cerebral spinal fluid, etc. These methods can be implemented in many different ways. For example, "comparing the structure" steps include, but are not limited to, comparing restriction maps, nucleotide sequences, amino acid sequences, RFLPs, Dnase sites, DNA methylation fingerprints (e.g., U.S. Pat. No. 6,214,556), protein cleavage sites, molecular weights, electrophoretic mobilities, charges, ion mobility, etc., between a standard gene and a test gene. The term "structure" can refer to any physical characteristics or configurations which can be used to distinguish between nucleic acids and polypeptides. The methods and instruments used to accomplish the comparing step depends upon the physical characteristics which are to be compared. Thus, various techniques are contemplated, including, e.g., sequencing machines (both amino acid and polynucleotide), electrophoresis, mass spectrometer (U.S. Pat. Nos. 6,093, 541, 6,002,127), liquid chromatography, HPLC, etc.

To carry out such methods, "all or part" of the gene or polypeptide can be compared. For example, if nucleotide sequencing is utilized, the entire gene can be sequenced, including promoter, introns, and exons, or only parts of it can be sequenced and compared, e.g., regions corresponding to 317–398, 317–366, 367–398, etc.

Mutagenesis

Mutated polynucleotide sequences of the present invention are useful for various purposes, e.g., to create mutations of the polypeptides they encode, to identify functional regions of genomic DNA, to produce probes for screening libraries, etc. Mutagenesis can be carried out routinely according to any effective method, e.g., oligonucleotide-directed (Smith, M., *Ann. Rev. Genet.* 19:423–463, 1985), degenerate oligonucleotide-directed (Hill et al., *Method Enzymology*, 155:558–568, 1987), region-specific (Myers et al., *Science*, 229:242–246, 1985; Derbyshire et al., *Gene*, 46:145, 1986; Ner et al., *DNA*, 7:127, 1988), linker-scanning (McKnight and Kingsbury, *Science*, 217:316–324, 1982), directed using PCR, recursive ensemble mutagenesis (Arkin and Yourvan, *Proc. Natl. Acad. Sci.*, 89:7811–7815, 1992), random mutagenesis (e.g., U.S. Pat. Nos. 5,096,815; 5,198, 346; and 5,223,409), site-directed mutagenesis (e.g., Walder et al., *Gene*, 42:133, 1986; Bauer et al., *Gene*, 37:73, 1985; Craik, *Bio Techniques*, Jan. 1985, 12–19, Smith et al., *Genetic Engineering: Principles and Methods*, Plenum Press, 1981), phage display (e.g., Lowman et al., *Biochem.* 30:10832–10837, 1991; Ladner et al., U.S. Pat. No. 5,223, 409; Huse, WIPO Publication WO 92/06204), etc. Desired sequences can also be produced by the assembly of target sequences using mutually priming oligonucleotides (Uhlmann, *Gene*, 71:29–40, 1988). For directed mutagenesis methods, analysis of the three-dimensional structure of the polypeptide can be used to guide and facilitate making mutants which effect polypeptide activity. Sites of substrate-enzyme interaction or other biological activities can also be determined by analysis of crystal structure as determined by such techniques as nuclear magnetic resonance, crystallography or photoaffinity labeling. See, for example, de Vos et al., Science 255:306–312, 1992; Smith et al., J. Mol. Biol. 224:899–904, 1992; Wlodaver et at., FEBS Lett. 309:59–64, 1992.

In addition, libraries of the gene and fragments thereof can be used for screening and selection of gene variants. For instance, a library of coding sequences can be generated by treating a double-stranded DNA with a nuclease under conditions where the nicking occurs, e.g., only once per molecule, denaturing the double-stranded DNA, renaturing it to for double-stranded DNA that can include sense/antisense pairs from different nicked products, removing single-stranded portions from reformed duplexes by treatment with S1 nuclease, and ligating the resulting DNAs into an expression vecore. By this method, xpression libraries can be made comprising "mutagenized" gene. The entire coding sequence or parts thereof can be used.

Polynucleotide Expression, Polypeptides Produced Thereby, and Specific-Binding Partners Thereto.

A polynucleotide according to the present invention can be expressed in a variety of different systems, in vitro and in vivo, according to the desired purpose. For example, a polynucleotide can be inserted into an expression vector, introduced into a desired host, and cultured under conditions effective to achieve expression of a polypeptide coded for by the polynucleotide, to search for specific binding partners. Effective conditions include any culture conditions which are suitable for achieving production of the polypeptide by the host cell, including effective temperatures, pH, medium, additives to the media in which the host cell is cultured (e.g., additives which amplify or induce expression such as butyrate, or methotrexate if the coding polynucleotide is adjacent to a dhfr gene), cycloheximide, cell densities, culture dishes, etc. A polynucleotide can be introduced into the cell by any effective method including, e.g., naked DNA, calcium phosphate precipitation, electroporation, injection, DEAE-Dextran mediated transfection, fusion with liposomes, association with agents which enhance its uptake into cells, viral transfection. A cell into which a polynucleotide of the present invention has been introduced is a transformed host cell. The polynucleotide can be extrachromosomal or integrated into a chromosome(s) of the host cell. It can be stable or transient. An expression vector is selected for its compatibility with the host cell. Host cells include, mammalian cells, e.g., INSERT insect cells, such as Sf9 (S. frugipeda) and Drosophila, bacteria, such as *E. coli*, Streptococcus, bacillus, yeast, such as Sacharomyces, *S. cerevisiae*, fungal cells, plant cells, embryonic or adult stem cells (e.g., mammalian, such as mouse or human).

Expression control sequences are similarly selected for host compatibility and a desired purpose, e.g., high copy number, high amounts, induction, amplification, controlled expression. Other sequences which can be employed include enhancers such as from SV40, CMV, RSV, inducible promoters, cell-type specific elements, or sequences which allow selective or specific cell expression. Promoters that can be used to drive its expression, include, e.g., the endogenous promoter, MMTV, SV40, trp, lac, tac, or T7 promoters for bacterial hosts; or alpha factor, alcohol oxidase, or PGH promoters for yeast. RNA promoters can be used to produced RNA transcripts, such as T7 or SP6. See, e.g., Melton et al., *Polynucleotide Res.*, 12(18):7035–7056, 1984; Dunn and Studier. *J. Mol. Bio.*, 166:477–435, 1984; U.S. Pat. No. 5,891,636; Studier et al., *Gene Expression Technology, Methods in Enzymology,* 85:60–89, 1987. In addition, as discussed above, translational signals (including in-frame insertions) can be included.

When a polynucleotide is expressed as a heterologous gene in a transfected cell line, the gene is introduced into a cell as described above, under effective conditions in which the gene is expressed. The term "heterologous" means that the gene has been introduced into the cell line by the "hand-of-man." Introduction of a gene into a cell line is discussed above. The transfected (or transformed) cell expressing the gene can be lysed or the cell line can be used intact.

For expression and other purposes, a polynucleotide can contain codons found in a naturally-occurring gene, transcript, or cDNA, for example, e.g., as set forth in SEQ ID NO 1, or it can contain degenerate codons coding for the same amino acid sequences. For instance, it may be desirable to change the codons in the sequence to optimize the sequence for expression in a desired host. See, e.g., U.S. Pat. Nos. 5,567,600 and 5,567,862.

A polypeptide according to the present invention can be recovered from natural sources, transformed host cells (culture medium or cells) according to the usual methods, including, detergent extraction (e.g., non-ionic detergent, Triton X-100, CHAPS, octylglucoside, Igepal CA-630), ammonium sulfate or ethanol precipitation, acid extraction, anion or cation exchange chromatography, phosphocellulose chromatography, hydrophobic interaction chromatography, hydroxyapatite chromatography, lectin chromatography, gel electrophoresis. Protein refolding steps can be used, as necessary, in completing the configuration of the mature protein. Finally, high performance liquid chromatography (HPLC) can be employed for purification steps. Another approach is express the polypeptide recombinantly with an affinity tag (Flag epitope, HA epitope, myc epitope, 6×His, maltose binding protein, chitinase, etc) and then purify by anti-tag antibody-conjugated affinity chromatography.

The present invention also relates to antibodies, and other specific-binding partners, which are specific for polypeptides encoded by polynucleotides of the present invention. Antibodies, e.g., polyclonal, monoclonal, recombinant, chimeric, humanized, single-chain, Fab, and fragments thereof, can be prepared according to any desired method. See, also, screening recombinant immunoglobulin libraries (e.g., Orlandi et al., *Proc. Natl. Acad. Sci.*, 86:3833–3837, 1989; Huse et al., *Science*, 256:1275–1281, 1989); in vitro stimulation of lymphocyte populations; Winter and Milstein, *Nature,* 349: 293–299, 1991. The antibodies can be IgM, IgG, subtypes, IgG2a, IgG1, etc. Antibodies, and immune responses, can also be generated by administering naked DNA See, e.g., U.S. Pat. Nos. 5,703,055; 5,589,466; 5,580,859. Antibodies can be used from any source, including, goat, rabbit, mouse, chicken (e.g., IgY; see, Duan, W0/029444 for methods of making antibodies in avian hosts, and harvesting the antibodies from the eggs). An antibody specific for a polypeptide means that the antibody recognizes a defined sequence of amino acids within or including the polypeptide. Other specific binding partners include, e.g., aptamers and PNA. antibodies can be prepared against specific epitopes or domains as set forth in Table 2.

The preparation of polyclonal antibodies is well-known to those skilled in the art. See, for example, Green et al., Production of Polyclonal Antisera, in IMMUNOCHEMICAL PROTOCOLS (Manson, ed.), pages 1–5 (Humana Press 1992); Coligan et al., Production of Polyclonal Antisera in Rabbits, Rats, Mice and Hamsters, in CURRENT PROTOCOLS IN IMMUNOLOGY, section 2.4.1 (1992). The preparation of monoclonal antibodies likewise is conventional. See, for example, Kohler & Milstein, Nature 256:495 (1975); Coligan et al., sections 2.5.1–2.6.7; and Harlow et al., ANTIBODIES: A LABORATORY MANUAL, page 726 (Cold Spring Harbor Pub. 1988).

Antibodies can also be humanized, e.g., where they are to be used therapeutically. Humanized monoclonal antibodies are produced by transferring mouse complementarity determining regions from heavy and light variable chains of the mouse immunoglobulin into a human variable domain, and then substituting human residues in the framework regions of the murine counterparts. The use of antibody components derived from humanized monoclonal antibodies obviates potential problems associated with the immunogenicity of murine constant regions. General techniques for cloning murine immunoglobulin variable domains are described, for example, by Orlandi et al., Proc. Nat'l Acad. Sci. USA 86:3833 (1989), which is hereby incorporated in its entirety by reference. Techniques for producing humanized monoclonal antibodies are described, for example, in U.S. Pat. No. 6,054,297, Jones et al., Nature 321: 522 (1986); Riechmann et al., Nature 332: 323 (1988); Verhoeyen et al., Science 239: 1534 (1988); Carter et al., Proc. Nat'l Acad. Sci. USA 89: 4285 (1992); Sandhu, Crit. Rev. Biotech. 12: 437 (1992); and Singer et al., J. Immunol. 150: 2844 (1993).

Antibodies of the invention also may be derived from human antibody fragments isolated from a combinatorial immunoglobulin library. See, for example, Barbas et al., METHODS: A COMPANION TO METHODS IN ENZYMOLOGY, VOL. 2, page 119 (1991); Winter et al., Ann. Rev. Immunol. 12: 433 (1994). Cloning and expression vectors that are useful for producing a human immunoglobulin phage library can be obtained commercially, for example, from STRATAGENE Cloning Systems (La Jolla, Calif.).

In addition, antibodies of the present invention may be derived from a human monoclonal antibody. Such antibodies can be obtained from transgenic mice that have been "engineered" to produce specific human antibodies in response to antigenic challenge. In this technique, elements of the human heavy and light chain loci are introduced into strains of mice derived from embryonic stem cell lines that contain targeted disruptions of the endogenous heavy and light chain loci. The transgenic mice can synthesize human antibodies specific for human antigens and can be used to produce human antibody-secreting hybridomas. Methods for obtaining human antibodies from transgenic mice are described, e.g., in Green et al., Nature Genet. 7:13 (1994); Lonberg et al., Nature 368:856 (1994); and Taylor et al., Int. Immunol. 6:579 (1994).

Antibody fragments of the present invention can be prepared by proteolytic hydrolysis of the antibody or by expression in E. coli of nucleic acid encoding the fragment. Antibody fragments can be obtained by pepsin or papain digestion of whole antibodies by conventional methods. For example, antibody fragments can be produced by enzymatic cleavage of antibodies with pepsin to provide a 5S fragment denoted F(ab').sub.2. This fragment can be further cleaved using a thiol reducing agent, and optionally a blocking group for the sulfhydryl groups resulting from cleavage of disulfide linkages, to produce 3.5S Fab' monovalent fragments. Alternatively, an enzymatic cleavage using pepsin produces two monovalent Fab' fragments and an Fc fragment directly. These methods are described, for example, by Goldenberg, U.S. Pat. No. 4,036,945 and No. 4,331,647, and references contained therein. These patents are hereby incorporated in their entireties by reference. See also Nisoiihoff et al., Arch. Biochem. Biophys. 89:230 (1960); Porter, Biochem. J. 73:119 (1959); Edelman et al, METHODS IN ENZYMOLOGY, VOL. 1, page 422 (Academic Press 1967); and Coligan et al. at sections 2.8.1–2.8.10 and 2.10.1–2.10.4.

Other methods of cleaving antibodies, such as separation of heavy chains to form monovalent light-heavy chain fragments, further cleavage of fragments, or other enzymatic, chemical, or genetic techniques can also be used. For example, Fv fragments comprise an association of V.sub.H and V.sub.L chains. This association may be noncovalent, as described in Inbar et al., Proc. Nat'l Acad. Sci. USA 69:2659 (1972). Alternatively, the variable chains can be linked by an intermolecular disulfide bond or cross-linked by chemicals such as glutaraldehyde. See, e.g., Sandhu, supra. Preferably, the Fv fragments comprise V.sub.H and V. sub.L chains connected by a peptide linker. These single-chain antigen binding proteins (sFv) are prepared by constructing a structural gene comprising nucleic acid sequences encoding the V.sub.H and V.sub.L domains connected by an oligonucleotide. The structural gene is inserted into an expression vector, which is subsequently introduced into a host cell such as E. coli. The recombinant host cells synthesize a single polypeptide chain with a linker peptide bridging the two V domains. Methods for producing sFvs are described, for example, by Whitlow et al., METHODS: A COMPANION TO METHODS IN ENZYMOLOGY, VOL. 2, page 97 (1991); Bird etal., Science 242:423–426 (1988); Ladner et al., U.S. Pat. No. 4,946,778; Pack et al., Bio/Technology 11: 1271–77 (1993); and Sandhu, supra.

Another form of an antibody fragment is a peptide coding for a single complementarity-determining region (CDR). CDR peptides ("minimal recognition units") can be obtained by constructing genes encoding the CDR of an antibody of interest. Such genes are prepared, for example, by using the polymerase chain reaction to synthesize the variable region from RNA of antibody-producing cells. See, for example, Larrick et al., METHODS: A COMPANION TO METHODS IN ENZYMOLOGY, VOL. 2, page 106 (1991).

The term "antibody" as used herein includes intact molecules as well as fragments thereof, such as Fab, F(ab')2, and Fv which are capable of binding to an epitopic determinant present in Bin1 polypeptide. Such antibody fragments retain some ability to selectively bind with its antigen or receptor. The term "epitope" refers to an antigenic determinant on an antigen to which the paratope of an antibody binds. Epitopic determinants usually consist of chemically active surface groupings of molecules such as amino acids or sugar side chains and usually have specific three dimensional structural characteristics, as well as specific charge characteristics. Antibodies can be prepared against specific epitopes or polypeptide domains.

Antibodies which bind to polypeptides of the present invention can be prepared using an intact polypeptide or fragments containing small peptides of interest as the immunizing antigen. For example, it may be desirable to produce antibodies that specifically bind to the N- or C-terminal domains. The polypeptide or peptide used to immunize an animal which is derived from translated cDNA or chemically synthesized which can be conjugated to a carrier protein, if desired. Such commonly used carriers which are chemically coupled to the immunizing peptide include keyhole limpet hemocyanin (KLH), thyroglobulin, bovine serum albumin (BSA), and tetanus toxoid.

Polyclonal or monoclonal antibodies can be further purified, for example, by binding to and elution from a matrix to which the polypeptide or a peptide to which the antibodies were raised is bound. Those of skill in the art will know of various techniques common in the immunology arts for purification and/or concentration of polyclonal antibodies, as well as monoclonal antibodies (See for example, Coligan, et al., Unit 9, Current Protocols in Immunology, Wiley Interscience, 1994, incorporated by reference).

Anti-idiotype technology can also be used to produce invention monoclonal antibodies which mimic an epitope. For example, an anti-idiotypic monoclonal antibody made to a first monoclonal antibody will have a binding domain in the hypervariable region which is the "image" of the epitope bound by the first monoclonal antibody.

Methods of Detecting Polypeptides

Polypeptides coded for by genes of the present invention can be detected, visualized, determined, quantitated, etc. according to any effective method. useful methods include, e.g., but are not limited to, immunoassays, RIA (radioimmunassay), ELISA, (enzyme-linked-immunosorbent assay), immunoflourescence, flow cytometry, histology, electron microscopy, light microscopy, in situ assays, immunoprecipitation, Western blot, immunocytochemistry.

Immunoassays may be carried in liquid or on biological support. For instance, a sample (e.g., blood, stool, urine, cells, tissue, cerebral spinal fluid, body fluids, etc.) can be brought in contact with and immobilized onto a solid phase support or carrier such as nitrocellulose, or other solid support that is capable of immobilizing cells, cell particles or soluble proteins. The support may then be washed with suitable buffers followed by treatment with the detectably labeled gene specific antibody. The solid phase support can then be washed with a buffer a second time to remove unbound antibody. The amount of bound label on solid support may then be detected by conventional means.

A "solid phase support or carrier" includes any support capable of binding an antigen, antibody, or other specific binding partner. Supports or carriers include glass, polystyrene, polypropylene, polyethylene, dextran, nylon, amylases, natural and modified celluloses, polyacrylamides, and magnetite. A support material can have any structural or physical configuration. Thus, the support configuration may be spherical, as in a bead, or cylindrical, as in the inside surface of a test tube, or the external surface of a rod. Alternatively, the surface may be flat such as a sheet, test strip, etc. Preferred supports include polystyrene beads One of the many ways in which gene peptide-specific antibody can be detectably labeled is by linking it to an enzyme and using it in an enzyme immunoassay (EIA). See, e.g., Voller, A., "The Enzyme Linked Immunosorbent Assay (ELISA)," 1978, Diagnostic Horizons 2, 1–7, Microbiological Associates Quarterly Publication, Walkersville, Md.); Voller, A. et al., 1978, J. Clin. Pathol. 31, 507–520; Butler, J. E., 1981, Meth. Enzymol. 73, 482–523; Maggio, E. (ed.), 1980, Enzyme Immunoassay, CRC Press, Boca Raton, Fla.. The enzyme which is bound to the antibody will react with an appropriate substrate, preferably a chromogenic substrate, in such a manner as to produce a chemical moiety that can be detected, for example, by spectrophotometric, fluorimetric or by visual means. Enzymes that can be used to detectably label the antibody include, but are not limited to, malate dehydrogenase, staphylococcal nuclease, delta-5-steroid isomerase, yeast alcohol dehydrogenase, alpha.-glycerophosphate, dehydrogenase, triose phosphate isomerase, horseradish peroxidase, alkaline phosphatase, asparaginase, glucose oxidase, beta.-galactosidase, ribonuclease, urease, catalase, glucose-6-phosphate dehydrogenase, glucoamylase and acetylcholinesterase. The detection can be accomplished by colorimetric methods that employ a chromogenic substrate for the enzyme. Detection may also be accomplished by visual comparison of the extent of enzymatic reaction of a substrate in comparison with similarly prepared standards.

Detection may also be accomplished using any of a variety of other immunoassays. For example, by radioactively labeling the antibodies or antibody fragments, it is possible to detect peptides through the use of a radioimmunoassay (RIA). See, e.g., Weintraub, B., Principles of Radioimmunoassays, Seventh Training Course on Radioligand Assay Techniques, The Endocrine Society, March, 1986. The radioactive isotope can be detected by such means as the use of a gamma counter or a scintillation counter or by autoradiography.

It is also possible to label the antibody with a fluorescent compound. When the fluorescently labeled antibody is exposed to light of the proper wave length, its presence can then be detected due to fluorescence. Among the most commonly used fluorescent labeling compounds are fluorescein isothiocyanate, rhodamine, phycoerythrin, phycocyanin, allophycocyanin, o-phthaldehyde and fluorescamine. The antibody can also be detectably labeled using fluorescence emitting metals such as those in the lanthanide series. These metals can be attached to the antibody using such metal chelating groups as diethylenetriaminepentacetic acid (DTPA) or ethylenediaminetetraacetic acid (EDTA).

The antibody also can be detectably labeled by coupling it to a chemiluminescent compound. The presence of the chemiluminescent-tagged antibody is then determined by detecting the presence of luminescence that arises during the course of a chemical reaction. Examples of useful chemiluminescent labeling compounds are luminol, isoluminol, theromatic acridinium ester, imidazole, acridinium salt and oxalate ester.

Likewise, a bioluminescent compound may be used to label the antibody of the present invention. Bioluminescence is a type of chemiluminescence found in biological systems in which a catalytic protein increases the efficiency of the chemiluminescent reaction. The presence of a bioluminescent protein is determined by detecting the presence of luminescence. Important bioluminescent compounds for purposes of labeling are luciferin, luciferase and aequorin.

Diagnostic

The present invention also relates to methods and compositions for diagnosing a disorder or condition associated with melanocortin receptor 1C, or determining susceptibility to a disorder or condition, using polynucleotides, polypeptides, and specific-binding partners of the present invention to detect, assess, determine, etc., MCR-1C In such methods, the gene can serve as a marker for the disorder or condition, e.g., where the gene, when mutant, is a direct cause of the disorder; where the gene is affected by another gene(s) which is directly responsible for the disorder, e.g., when the gene is part of the same signaling pathway as the directly responsible gene; and, where the gene is chromosomally linked to the gene(s) directly responsible for the disorder, and segregates with it. Many other situations are possible. To detect, assess, determine, etc., a probe specific for the gene can be employed as described above and below. Any method of detecting and/or assessing the gene can be used, including detecting expression of the gene using polynucleotides, antibodies, or other specific-binding partners. Diseases and conditions, include melanoma, UV-sensitivity, inflammation, etc., and include genetic diagnosis for any purpose, including to select traits and phenotypes, such as skin and hair color.

The present invention relates to methods of diagnosing disorders or conditions associated with a melanocortin receptor gene of the present invention, or determining a subject's susceptibility to such disorder, comprising, e.g., assessing the expression of a gene in a tissue sample comprising tissue or cells suspected of having the disorder (e.g., where the sample comprises thymus or bone marrow tissues). The phrase "diagnosing" indicates that it is determined whether the sample has the disorder. A "disorder" means, e.g., any abnormal condition as in a disease or malady. "Determining a subject's susceptibility to a disease or disorder" indicates that the subject is assessed for whether s/he is predisposed to get such a disease or disorder, where the predisposition is indicated by abnormal expression of the gene (e.g., gene mutation, gene expression pattern is not normal, etc.). Predisposition or susceptibility to a disease may result when a such disease is influenced by epigenetic, environmental, etc., factors. This includes prenatal screening where samples from the fetus or embryo (e.g., via amniocentesis or CV sampling) are analyzed for the expression of the gene.

By the phrase "assessing expression of gene," it is meant that the functional status of the gene is evaluated. This includes, but is not limited to, measuring expression levels of said gene, determining the genomic structure of said gene, determining the mRNA structure of transcripts from said gene, or measuring the expression levels of polypeptide coded for by said gene. Thus, the term "assessing expression" includes evaluating the all aspects of the transcriptional and translational machinery of the gene. For instance, if a promoter defect causes, or is suspected of causing, the disorder, then a sample can be evaluated (i.e., "assessed") by looking (e.g., sequencing or restriction mapping) at the promoter sequence in the gene, by detecting transcription products (e.g., RNA), by detecting translation product (e.g., polypeptide). Any measure of whether the gene is functional can be used, including, polypeptide, polynucleotide, and functional assays for the gene's biological activity.

In making the assessment, it can be useful to compare the results to a normal gene, e.g., a gene which is not associated with the disorder. The nature of the comparison can be determined routinely, depending upon how the assessing is accomplished. If, for example, the mRNA levels of a sample is detected, then the mRNA levels of a normal can serve as a comparison, or a gene which is known not to be affected by the disorder. Methods of detecting mRNA are well known, and discussed above, e.g., but not limited to, Northern blot analysis, polymerase chain reaction (PCR), reverse transcriptase PCR, RACE PCR, etc. Similarly, if polypeptide production is used to evaluate the gene, then the polypeptide in a normal tissue sample can be used as a comparison, or, polypeptide from a different gene whose expression is known not to be affected by the disorder. These are only examples of how such a method could be carried out.

Assessing the effects of therapeutic and preventative interventions (e.g., administration of a drug, chemotherapy, radiation, etc.) on immune system disorders is a major effort in drug discovery, clinical medicine, and pharmacogenomics. The evaluation of therapeutic and preventative measures, whether experimental or already in clinical use, has broad applicability, e.g., in clinical trials, for monitoring the status of a patient, for analyzing and assessing animal models, and in any scenario involving cancer treatment and prevention. Analyzing the expression profiles of polynucleotides of the present invention can be utilized as a parameter by which interventions are judged and measured. Treatment of a disorder can change the expression profile in some manner which is prognostic or indicative of the drug's effect on it. Changes in the profile can indicate, e.g., drug toxicity, return to a normal level, etc. Accordingly, the present invention also relates to methods of monitoring or assessing a therapeutic or preventative measure (e.g., chemotherapy, radiation, anti-neoplastic drugs, antibodies, etc.) in a subject having a melanoma, or other disorder or condition comprising a tissue in which MCR-1C is expressed, or who is susceptible to such a disorder or condition, comprising, e.g., detecting the expression levels of a melanocortin receptor gene of the present invention. A subject can be a cell-based assay system, non-human animal model, human patient, etc. Detecting can be accomplished as described for the methods above and below. By "therapeutic or preventative intervention," it is meant, e.g., a drug administered to a patient, surgery, radiation, chemotherapy, and other measures taken to prevent, treat, or diagnose a disorder.

Expression can be assessed in any sample comprising any tissue or cell type, body fluid, etc., as discussed for other methods of the present invention, including cells from thymus, bone marrow, lung, muscle, and peripheral blood cells.

The present invention also relates to methods of using binding partners, such as antibodies, to deliver active agents to any of the tissues in which a MCR-1C receptor of the present invention is expressed, for a variety of different purposes, including, e.g., for diagnostic, therapeutic (e.g., to treat melanoma), and research purposes. Methods can involve delivering or administering an active agent to melanocytes, comprising, e.g., administering to a subject in need thereof, an effective amount of an active agent coupled to a binding partner specific for a polypeptide, wherein said binding partner is effective to deliver said active agent specifically to said cells.

Any type of active agent can be used, including, therapeutic, cytotoxic, cytostatic, chemotherapeutic, anti-neoplastic, anti-proliferative, anti-biotic, etc., agents. A chemotherapeutic agent can be, e.g., DNA-interactive agent, alkylating agent, antimetabolite, tubulin-interactive agent, hormonal agent, hydroxyurea, Cisplatin, Cyclophosphamide, Altretamine, Bleomycin, Dactinomycin, Doxorubicin, Etoposide, Teniposide, paclitaxel, cytoxan, 2-methoxycarbonylaminobenzimidazole, Plicamycin, Methotrexate, Fluorouracil, Fluorodeoxyuridin, CB3717, Azacitidine, Floxuridine, Mercapyopurine, 6-Thioguanine, Pentostatin, Cytarabine, Fludarabine, etc. Agents can also be contrast agents useful in imaging technology, e.g., X-ray, CT, CAT, MRI, ultrasound, PET, SPECT, and scintographic.

An active agent can be associated in any manner with a binding partner which is effective to achieve its delivery specifically to the target. Specific delivery or targeting indicates that the agent is provided to the intended tissue, without being substantially provided to other tissues. This is useful especially where an agent is toxic, and specific targeting to the intended tissue enables the majority of the toxicity to be aimed at it, with as small as possible effect on other tissues in the body. The association of the active agent and the binding partner ("coupling) can be direct, e.g., through chemical bonds between the binding partner and the agent, or, via a linking agent, or the association can be less direct, e.g., where the active agent is in a liposome, or other carrier, and the binding partner is associated with the liposome surface. In such case, the binding partner can be oriented in such a way that it is able to bind to the polypeptide on the cell surface. Methods for delivery of DNA via a cell-surface receptor is described, e.g., in U.S. Pat. No. 6,339,139.

Identifying Agent Methods

The present invention also relates to methods of identifying agents, and the agents themselves, which modulate a melanocortin receptor gene of the present invention. These agents can be used to modulate the biological activity of the polypeptide encoded for the gene, or the gene, itself. Agents which regulate the gene or its product are useful in variety of different environments, including as medicinal agents to treat or prevent disorders associated with a melanocortin receptor gene of the present invention and as research reagents to modify the function of tissues and cell. For examples of ligands, and methods of identifying agents, such as agonists and antagonists, that modulate melanocortin receptors, see, e.g., WO0039147, WO9957148, U.S. Pat. Nos. 5,731,408, 6,100,048, and 6,350,760. As discussed above, such agents can be useful to treat melanoma, to treat or enhance UV-sensitivity, to modulate skin or hair pigmentation, to change skin color, etc.

Methods of identifying agents generally comprise steps in which an agent is placed in contact with the gene, transcription product, translation product, or other target, and then a determination is performed to assess whether the agent "modulates" the target. The specific method utilized will depend upon a number of factors, including, e.g., the target (i.e., is it the gene or polypeptide encoded by it), the environment (e.g., in vitro or in vivo), the composition of the agent, etc.

For modulating the expression of a melanocortin receptor gene of the present invention, a method can comprise, in any effective order, one or more of the following steps, e.g., contacting a gene (e.g., in a cell population) with a test agent under conditions effective for said test agent to modulate the expression of a melanocortin receptor gene of the present invention, and determining whether said test agent modulates said gene. An agent can modulate expression of a melanocortin receptor gene of the present invention at any level, including transcription, translation, and/or perdurance of the nucleic acid (e.g., degradation, stability, etc.) in the cell.

For modulating the biological activity of polypeptides coded for by a melanocortin receptor gene of the present invention, a method can comprise, in any effective order, one or more of the following steps, e.g., contacting a polypeptide (e.g., in a cell, lysate, or isolated) with a test agent under conditions effective for said test agent to modulate the biological activity of said polypeptide, and determining whether said test agent modulates said biological activity.

Contacting the gene or polypeptide with the test agent can be accomplished by any suitable method and/or means that places the agent in a position to functionally control expression or biological activity of the gene or polypeptide present in the sample. Functional control indicates that the agent can exert its physiological effect on the gene or polypeptide through whatever mechanism it works. The choice of the method and/or means can depend upon the nature of the agent and the condition and type of environment in which the gene or polypeptide is presented, e.g., lysate, isolated, or in a cell population (such as, in vivo, in vitro, organ explants, etc.). For instance, if the cell population is an in vitro cell culture, the agent can be contacted with the cells by adding it directly into the culture medium. If the agent cannot dissolve readily in an aqueous medium, it can be incorporated into liposomes, or another lipophilic carrier, and then administered to the cell culture. Contact can also be facilitated by incorporation of agent with carriers and delivery molecules and complexes, by injection, by infusion, etc.

After the agent has been administered in such a way that it can gain access to the gene or polypeptide, it can be determined whether the test agent modulates gene expression or polypeptide biological activity. Modulation can be of any type, quality, or quantity, e.g., increase, facilitate, enhance, up-regulate, stimulate, activate, amplify, augment, induce, decrease, down-regulate, diminish, lessen, reduce, etc. The modulatory quantity can also encompass any value, e.g., 1%, 5%, 10%, 50%, 75%, 1-fold, 2-fold, 5-fold, 10-fold, 100-fold etc. To modulate expression means, e.g., that the test agent has an effect on its expression, e.g., to effect the amount of transcription, to effect RNA splicing, to effect translation of the RNA into polypeptide, to effect RNA or polypeptide stability, to effect polyadenylation or other processing of the RNA, to effect post-transcriptional or post-translational processing, etc. To modulate biological activity means, e.g., that a functional activity of the polypeptide is changed in comparison to its normal activity in the absence of the agent. This effect includes, increase, decrease, block, inhibit, enhance, etc. Biological activities of GPCR, include, e.g., ligand binding and signal transduction activity.

A test agent can be of any molecular composition, e.g., chemical compounds, biomolecules, such as polypeptides, lipids, nucleic acids (e.g., antisense to a polynucleotide sequence selected SEQ ID NO 1), carbohydrates, antibodies, ribozymes, double-stranded RNA, aptamers, etc. For example, if a polypeptide to be modulated is a cell-surface molecule, a test agent can be an antibody that specifically recognizes it and, e.g., causes the polypeptide to be internalized, leading to its down regulation on the surface of the cell. Such an effect does not have to be permanent, but can require the presence of the antibody to continue the down-regulatory effect. Antibodies can also be used to modulate the biological activity a polypeptide in a lysate or other cell-free form. Antisense can also be used as test agents to modulate gene expression.

Therapeutics

Selective polynucleotides, polypeptides, and specific-binding partners thereto, can be utilized in therapeutic applications, especially to treat diseases and conditions of the immune system. Useful methods include, but are not limited to, immunotherapy (e.g., using specific-binding partners to polypeptides), vaccination (e.g., using a selective polypeptide or a naked DNA encoding such polypeptide), protein or polypeptide replacement therapy, gene therapy (e.g., germ-line correction, antisense), etc.

Various immunotherapeutic approaches can be used. For instance, unlabeled antibody that specifically recognizes a tissue-specific antigen can be used to stimulate the body to destroy or attack the melanoma, cancer, or other melanocyte growth, to cause down-regulation, to produce complement-mediated lysis, to inhibit cell growth etc., of target cells which display the antigen, e.g., analogously to how c-erbB-2 antibodies are used to treat breast cancer. In addition, antibody can be labeled or conjugated to enhance its deleterious effect, e.g., with radionuclides and other energy emitting entitities, toxins, such as ricin, exotoxin A (ETA), and diphtheria, cytotoxic or cytostatic agents, immuno-modulators, chemotherapeutic agents, etc. See, e.g., U.S. Pat. No. 6,107,090.

An antibody or other specific-binding partner can be conjugated to a second molecule, such as a cytotoxic agent, and used for targeting the second molecule to a tissue-antigen positive cell (Vitetta, E. S. et al., 1993, Immunotoxin therapy, in DeVita, Jr., V. T. et al., eds, Cancer: Principles and Practice of Oncology, 4th ed., J.B. Lippincott Co., Philadelphia, 2624–2636). Examples of cytotoxic agents include, but are not limited to, antimetabolites, alkylating agents, anthracyclines, antibiotics, anti-mitotic agents, radioisotopes and chemotherapeutic agents. Further examples of cytotoxic agents include, but are not limited to ricin, doxorubicin, daunorubicin, taxol, ethidium bromide, mitomycin, etoposide, tenoposide, vincristine, vinblastine, colchicine, dihydroxy anthracin dione, actinomycin D, 1-de-hydrotestosterone, diptheria toxin, Pseudomonas exotoxin (PE) A, PE40, abrin, elongation factor-2 and glucocorticoid. Techniques for conjugating therapeutic agents to antibodies are well.

In addition to immunotherapy, polynucleotides and polypeptides can be used as targets for non-immunotherapeutic applications, e.g., using compounds which interfere with function, expression (e.g., antisense as a therapeutic agent), assembly, etc. RNA interference can be used in vitro and in vivo to silence gene when its expression contributes to a disease (but also for other purposes, e.g., to identify the gene's function to change a developmental pathway of a cell, etc.). See, e.g., Sharp and Zamore, *Science*, 287: 2431–2433, 2001; Grishok et al., *Science*, 287:2494, 2001.

Delivery of therapeutic agents can be achieved according to any effective method, including, liposomes, viruses, plasmid vectors, bacterial delivery systems, orally, systemically, etc. Therapeutic agents of the present invention can be administered in any form by any effective route, including, e.g., oral, parenteral, enteral, intraperitoneal, topical, transdermal (e.g., using any standard patch), intravenously, ophthalmic, nasally, local, non-oral, such as aerosal, inhalation, subcutaneous, intramuscular, buccal, sublingual, rectal, vaginal, intra-arterial, and intrathecal, etc. They can be administered alone, or in combination with any ingredient(s), active or inactive.

In addition to therapeutics, per se, the present invention also relates to methods of treating disorders or conditions showing altered expression of a melanocortin receptor gene of the present invention, comprising, e.g., administering to a subject in need thereof a therapeutic agent which is effective for regulating expression of said gene and/or which is effective in treating said disease. The term "treating" is used conventionally, e.g., the management or care of a subject for the purpose of combating, alleviating, reducing, relieving, improving the condition of, etc., of a disease or disorder. Diseases or disorders which can be treated in accordance with the present invention include those mentioned above for the thymus and bone marrow tissues.

By the phrase "altered expression," it is meant that the disease or condition is associated with a mutation in the gene, or any modification to the gene (or corresponding product) which affects its normal function. Thus, gene expression refers to, e.g., transcription, translation, splicing, stability of the mRNA or protein product, activity of the gene product, differential expression, etc.

Any agent which "treats" the disease can be used. Such an agent can be one which regulates the expression of the gene. Expression refers to the same acts already mentioned, e.g. transcription, translation, splicing, stability of the mRNA or protein product, activity of the gene product, differential expression, etc. For instance, if the condition was a result of a complete deficiency of the gene product, administration of gene product to a patient would be said to treat the disease and regulate the gene's expression. Many other possible situations are possible, e.g., where the gene is aberrantly expressed, and the therapeutic agent regulates the aberrant expression by restoring its normal expression pattern.

Antisense

Antisense polynucleotide (e.g., RNA) can also be prepared from a polynucleotide according to the present invention, preferably an anti-sense to a sequence of a melanocortin receptor gene of the present invention. Antisense polynucleotide can be used in various ways, such as to regulate or modulate expression of the polypeptides they encode, e.g., inhibit their expression, for in situ hybridization, for therapeutic purposes, for making targeted mutations (in vivo, triplex, etc.) etc. For guidance on administering and designing anti-sense, see, e.g., U.S. Pat. Nos. 6,200,960, 6,200,807, 6,197,584, 6,190,869, 6,190,661, 6,187,587, 6,168,950, 6,153,595, 6,150,162, 6,133,246, 6,117,847, 6,096,722, 6,087,343, 6,040,296, 6,005,095, 5,998,383, 5,994,230, 5,891,725, 5,885,970, and 5,840,708. An anti-sense polynucleotides can be operably linked to an expression control sequence. A total length of about 35 bp can be used in cell culture with cationic liposomes to facilitate cellular uptake, but for in vivo use, preferably shorter oligonucleotides are administered, e.g. 25 nucleotides.

Antisense polynucleotides can comprise modified, non-naturally-occurring nucleotides and linkages between the nucleotides (e.g., modification of the phosphate-sugar backbone; methyl phosphonate, phosphorothioate, or phosphorodithioate linkages; and 2'-O-methyl ribose sugar units), e.g., to enhance in vivo or in vitro stability, to confer nuclease resistance, to modulate uptake, to modulate cellular distribution and compartmentalization, etc. Any effective nucleotide or modification can be used, including those already mentioned, as known in the art, etc., e.g., disclosed in U.S. Pat. Nos. 6,133,438; 6,127,533; 6,124,445; 6,121,437; 5,218,103 (e.g., nucleoside thiophosphoramidites); 4,973,679; Sproat et al., "2'-O-Methyloligoribonucleotides: synthesis and applications," Oligonucleotides and Analogs A Practical Approach, Eckstein (ed.), IRL Press, Oxford, 1991, 49–86; Iribarren et al., "2'O-Alkyl Oligoribonucleotides as Antisense Probes," Proc. Natl. Acad. Sci. USA, 1990, 87, 7747–7751; Cotton et al., "2'-O-methyl, 2'-O-ethyl oligoribonucleotides and phosphorothioate oligodeoxyribonucleotides as inhibitors of the in vitro U7 snRNP-dependent mRNA processing event," Nucl. Acids Res., 1991, 19, 2629–2635.

Arrays

The present invention also relates to an ordered array of polynucleotide probes and specific-binding partners (e.g., antibodies) for determining gene expression in melanocytes, monocytes, or other tissues in which MCR-1C is expressed, comprising, one or more polynucleotide probes or specific binding partners associated with a solid support, wherein each probe is specific for a melanocortin receptor gene of the present invention, or a specific-binding partner which is specific for a polypeptide coded for be a melancortin receptor gene of the present invention.

The phrase "ordered array" indicates that the probes (included both polynucleotide probes and specific binding partners) in an identifiable or position-addressable pattern, e.g., such as the arrays disclosed in U.S. Pat. Nos. 6,156,501, 6,077,673, 6,054,270, 5,723,320, 5,700,637, WO0991971 1, WO00023803. The probes are associated with the solid support in any effective way. For instance, the probes can be bound to the solid support, either by polymerizing the probes on the substrate, or by attaching a probe to the substrate. Association can be, covalent, electrostatic, noncovalent, hydrophobic, hydrophilic, noncovalent, coordination, adsorbed, absorbed, polar, etc. When fibers or hollow filaments are utilized for the array, the probes can fill the hollow orifice, be absorbed into the solid filament, be attached to the surface of the orifice, etc. Probes can be of any effective size, sequence identity, composition, etc., as already discussed.

Transgenic animals

The present invention also relates to transgenic animals comprising a melanocortin-1C, or mammalian homologs thereof. Such genes, as discussed in more detail below, include, but are not limited to, functionally-disrupted genes, mutated genes, ectopically or selectively-expressed genes, inducible or regulatable genes, etc. These transgenic animals can be produced according to any suitable technique or method, including homologous recombination, mutagenesis (e.g., ENU, Rathkolb et al., *Exp. Physiol.*, 85(6):635–644, 2000), and the tetracycline-regulated gene expression system (e.g., U.S. Pat. No. 6,242,667). The term "gene" as used herein includes any part of a gene, i.e., regulatory sequences, promoters, enhancers, exons, introns, coding sequences, etc. The nucleic acid present in the construct or transgene can be naturally-occurring wild-type, polymorphic, or mutated. Where the animal is a non-human animal, its homolog can be used instead.

Along these lines, polynucleotides of the present invention can be used to create transgenic animals, e.g. a non-human animal, comprising at least one cell whose genome comprises a functional disruption of a MCR-1C gene, e.g., in any part of the gene which disrupts the expression of the region corresponding to amino acids 367–398. A transgenic animal with a disrupted melanocortin-1C receptor can have a pigmentation phenotype, e.g., red or fair hair.

By the phrases "functional disruption" or "functionally disrupted," it is meant that the gene does not express a biologically-active product. It can be substantially deficient in at least one functional activity coded for by the gene. Expression of a polypeptide can be substantially absent, i.e., essentially undetectable amounts are made. However, polypeptide can also be made, but which is deficient in activity, e.g., where only an amino-terminal portion of the gene product is produced.

The transgenic animal can comprise one or more cells. When substantially all its cells contain the engineered gene, it can be referred to as a transgenic animal "whose genome comprises" the engineered gene. This indicates that the endogenous gene loci of the animal has been modified and substantially all cells contain such modification.

Functional disruption of the gene can be accomplished in any effective way, including, e.g., introduction of a stop codon into any part of the coding sequence, e.g., to prevent expression of amino acids 367–398, such that the resulting polypeptide is biologically inactive or lacks one or more of its functional regions, introduction of a mutation into a promoter or other regulatory sequence that is effective to turn it off, or reduce transcription of the gene, insertion of an exogenous sequence into the gene which inactivates it (e.g., which disrupts the production of a biologically-active polypeptide or which disrupts the promoter or other transcriptional machinery), deletion of sequences from the gene, etc. Examples of transgenic animals having functionally disrupted genes are well known, e.g., as described in U.S. Pat. Nos. 6,239,326, 6,225,525, 6,207,878, 6,194,633, 6,187,992, 6,180,849, 6,177,610, 6,100,445, 6,087,555, 6,080,910, 6,069,297, 6,060,642, 6,028,244, 6,013,858, 5,981,830, 5,866,760, 5,859,314, 5,850,004, 5,817,912, 5,789,654, 5,777,195, and 5,569,824. A transgenic animal which comprises the functional disruption can also be referred to as a "knock-out" animal, since the biological activity of its genes has been "knocked-out." Knock-outs can be homozygous or heterozygous.

For creating functional disrupted genes, and other gene mutations, homologous recombination technology is of special interest since it allows specific regions of the genome to be targeted. Using homologous recombination methods, genes can be specifically-inactivated, specific mutations can be introduced, and exogenous sequences can be introduced at specific sites. These methods are well known in the art, e.g., as described in the patents above. See, also, Robertson, *Biol. Reproduc.*, 44(2):238–245, 1991. Generally, the genetic engineering is performed in an embryonic stem (ES) cell, or other pluripotent cell line (e.g., adult stem cells, EG cells), and that genetically-modified cell (or nucleus) is used to create a whole organism. Nuclear transfer can be used in combination with homologous recombination technologies.

For example, a gene locus can be disrupted in mouse ES cells using a positive-negative selection method (e.g., Mansour et al., *Nature*, 336:348–352, 1988). In this method, a targeting vector can be constructed which comprises a part of the gene to be targeted. A selectable marker, such as neomycin resistance genes, can be inserted into a gene exon present in the targeting vector, disrupting it. When the vector recombines with the ES cell genome, it disrupts the function of the gene. The presence in the cell of the vector can be determined by expression of neomycin resistance. See, e.g., U.S. Pat. No. 6,239,326. Cells having at least one functionally disrupted gene can be used to make chimeric and germline animals, e.g., animals having somatic and/or germ cells comprising the engineered gene. Homozygous knockout animals can be obtained from breeding heterozygous knock-out animals. See, e.g., U.S. Pat. No. 6,225,525.

A transgenic animal, or animal cell, lacking one or more functional genes of the present invention can be useful in a variety of applications, including, as an animal model for conditions and diseases associated with melanocortin-1C, for drug screening (e.g., by making a cell deficient in MCR-1C, the contribution of the activity remaining variants, such as MCR-1B and the 317-amino acid form, can be assessed), as a source of tissues deficient in one or more MCR-1 activities, and any of the utilities mentioned in any issued U.S. Patent on transgenic animals, including, U.S. Pat. Nos. 6,239,326, 6,225,525, 6,207,878, 6,194,633, 6,187,992, 6,180,849, 6,177,610, 6,100,445, 6,087,555, 6,080,910, 6,069,297, 6,060,642, 6,028,244, 6,013,858, 5,981,830, 5,866,760, 5,859,314, 5,850,004, 5,817,912, 5,789,654, 5,777,195, and 5,569,824. By knocking-out melanocortin receptor activity, e.g., one at a time, the physiological pathways in pigmentation can be can be dissected out and identified.

The present invention also relates to non-human, transgenic animal whose genome comprises recombinant nucleic acid operatively linked to an expression control sequence effective to express said coding sequence, e.g., in melanocytes. Such a transgenic animal can also be referred to as a "knock-in" animal since an exogenous gene has been introduced, stably, into its genome. A knock-in animal can be engineered using the methods described in Healy et al., *Hum. Mol. Genet.*, 10:2397–2402, 2001, for MCR1.

A recombinant nucleic acid refers to a gene which has been introduced into a target host cell and optionally modified, such as cells derived from animals, plants, bacteria, yeast, etc. A recombinant gene includes completely synthetic nucleic acid sequences, semi-synthetic nucleic acid sequences, sequences derived from natural sources, and chimeras thereof. "Operable linkage" has the meaning used through the specification, i.e., placed in a functional relationship with another nucleic acid. When a gene is operably linked to an expression control sequence, as explained above, it indicates that the gene (e.g., coding sequence) is joined to the expression control sequence (e.g., promoter) in such a way that facilitates transcription and translation of the coding sequence. As described above, the phrase "genome" indicates that the genome of the cell has been modified. In this case, the recombinant gene has been stably integrated into the genome of the animal. The nucleic acid (e.g., coding sequence) in operable linkage with the expression control sequence can also be referred to as a construct or transgene.

Any expression control sequence can be used depending on the purpose. For instance, if selective expression is desired, then expression control sequences which limit its expression can be selected. These include, e.g., tissue or cell-specific promoters, introns, enhancers, etc. For various methods of cell and tissue-specific expression, see, e.g., U.S. Pat. Nos. 6,215,040, 6,210,736, and 6,153,427. These also include the endogenous promoter, i.e., the coding sequence can be operably linked to its own promoter. Inducible and regulatable promoters can also be utilized.

The present invention also relates to a transgenic animal which contains a functionally disrupted and a transgene stably integrated into the animals genome. Such an animal can be constructed using combinations any of the above- and below-mentioned methods. Such animals have any of the aforementioned uses, including permitting the knock-out of the normal gene and its replacement with a mutated gene. Such a transgene can be integrated at the endogenous gene locus so that the functional disruption and "knock-in" are carried out in the same step. The animal's endogenous locus can be replaced with a continuous coding sequence for MCR-1C, such that only MCR-1C is expressed, and no other form, such as MCR-1B and the 317-amino acid form, are expressed In addition to the methods mentioned above, transgenic animals can be prepared according to known methods, including, e.g., by pronuclear injection of recombinant genes into pronuclei of 1-cell embryos, incorporating an artificial yeast chromosome into embryonic stem cells, gene targeting methods, embryonic stem cell methodology, cloning methods, nuclear transfer methods. See, also, e.g., U.S. Pat. Nos. 4,736,866; 4,873,191; 4,873,316; 5,082,779; 5,304,489; 5,174,986; 5,175,384; 5,175,385; 5,221,778; Gordon et al., Proc. Natl. Acad. Sci., 77:7380–7384, 1980; Palmiter et al., Cell, 41:343–345, 1985; Palmiter et al., Ann. Rev. Genet., 20:465–499, 1986; Askew et al., Mol. Cell. Bio., 13:4115–4124, 1993; Games et al. Nature, 373:523–527, 1995; Valancius and Smithies, Mol. Cell. Bio., 11: 1402–1408, 199 1; Stacey et al., Mol. Cell. Bio., 14:1009–1016, 1994; Hasty et al., Nature, 350:243–246, 1995; Rubinstein et al., Nucl. Acid Res., 21:2613–2617, 1993; Cibelli et al., Science, 280:1256–1258, 1998. For guidance on recombinase excision systems, see, e.g., U.S. Pat. Nos. 5,626,159, 5,527,695, and 5,434,066. See also, Orban, P. C., et al., "Tissue-and Site-Specific DNA Recombination in Transgenic Mice," Proc. Natl. Acad Sci. USA, 89:6861–6865 (1992); O'Gorman, S., et al., "Recombinase-Mediated Gene Activation and Site-Specific Integration in Mammalian Cells," Science, 251:1351–1355 (1991); Sauer, B., et al., "Cre-stimulated recombination at loxP-Containing DNA sequences placed into the mammalian genome," Polynucleotides Research, 17(1):147–161 (1989); Gagneten, S. et al. (1997) Nucl. Acids Res. 25:3326–3331; Xiao and Weaver (1997) Nucl. Acids Res. 25:2985–2991; Agah, R. et al. (1997) J. Clin. Invest. 100:169–179; Barlow, C. et al. (1997) Nucl. Acids Res. 25:2543–2545; Araki, K. et al. (1997) Nucl. Acids Res. 25:868–872; Mortensen, R. N. et al. (1992) Mol. Cell. Biol. 12:2391–2395 (G418 escalation method); Lakhlani, P. P. et al. (1997) Proc. Natl. Acad. Sci. USA 94:9950–9955 ("hit and run"); Westphal and Leder (1997) Curr. Biol. 7:530–533 (transposon-generated "knock-out" and "knock-in"); Templeton, N. S. et al. (1997) Gene Ther. 4:700–709 (methods for efficient gene targeting, allowing for a high frequency of homologous recombination events, e.g., without selectable markers); PCT International Publication WO 93/22443 (functionally-disrupted).

A polynucleotide according to the present invention can be introduced into any non-human animal, including a non-human mammal, mouse (Hogan et al., *Manipulating the Mouse Embryo: A Laboratory Manual, Cold Spring Harbor Laboratory*, Cold Spring Harbor, N.Y., 1986), pig (Hammer et al., Nature, 315:343–345, 1985), sheep (Hammer et al., Nature, 315:343–345, 1985), cattle, rat, or primate. See also, e.g., Church, 1987, Trends in Biotech. 5:13–19; Clark et al., Trends in Biotech. 5:20–24, 1987); and DePamphilis et al., BioTechniques, 6:662–680, 1988. Transgenic animals can be produced by the methods described in U.S. Pat. No. 5,994,618, and utilized for any of the utilities described therein.

Database

The present invention also relates to electronic forms of polynucleotides, polypeptides, etc., of the present invention, including computer-readable medium (e.g., magnetic, optical, etc., stored in any suitable format, such as flat files or hierarchical files) which comprise such sequences, or fragments thereof, e-commerce-related means, etc. Along these lines, the present invention relates to methods of retrieving gene sequences from a computer-readable medium, comprising, one or more of the following steps in any effective order, e.g., selecting a cell or gene expression profile, e.g., a profile that specifies that said gene is differentially expressed in bone marrow or thymus tissues, and retrieving said differentially expressed gene sequences, where the gene sequences comprise or consist of MCR-1C, such as SEQ ID NOS 1, 2, and polymorphisms and variations thereof.

A "gene expression profile" means the list of tissues, cells, etc., in which a defined gene is expressed (i.e, transcribed and/or translated). A "cell expression profile" means the genes which are expressed in the particular cell type. The profile can be a list of the tissues in which the gene is expressed, but can include additional information as well, including level of expression (e.g., a quantity as compared or normalized to a control gene), and information on temporal (e.g., at what point in the cell-cycle or developmental program) and spatial expression. By the phrase "selecting a gene or cell expression profile," it is meant that a user decides what type of gene or cell expression pattern he is interested in retrieving, e.g., he may require that the gene is differentially expressed in a tissue, or he may require that the gene is not expressed in peripheral blood, but must be expressed in bone marrow or thymus. Any pattern of expression preferences may be selected. The selecting can be performed by any effective method. In general, "selecting" refers to the process in which a user forms a query that is used to search a database of gene expression profiles. The step of retrieving involves searching for results in a database that correspond to the query set forth in the selecting step. Any suitable algorithm can be utilized to perform the search query, including algorithms that look for matches, or that perform optimization between query and data. The database is information that has been stored in an appropriate storage medium, having a suitable computer-readable format. Once results are retrieved, they can be displayed in any suitable format, such as HTML.

For instance, the user may be interested in identifying genes that are differentially expressed in a melanocytes or another tissue. He may not care whether small amounts of expression occur in other tissues. A query is formed by the user to retrieve the set of genes from the database having the desired gene or cell expression profile. Once the query is inputted into the system, a search algorithm is used to interrogate the database, and retrieve results.

Advertising, Licensing, etc., Methods

The present invention also relates to methods of advertising, licensing, selling, purchasing, brokering, etc., genes, polynucleotides, specific-binding partners, antibodies, etc., of the present invention. Methods can comprises, e.g., displaying a gene or polypeptide for MCR-1C in a printed or computer-readable medium (e.g., on the Web or Internet), accepting an offer to purchase said gene, polypeptide, or antibody.

Other

A polynucleotide, probe, polypeptide, antibody, specific-binding partner, etc., according to the present invention can be isolated. The term "isolated" means that the material is in a form in which it is not found in its original environment or in nature, e.g., more concentrated, more purified, separated from component, etc. An isolated polynucleotide includes, e.g., a polynucleotide having the sequenced separated from the chromosomal DNA found in a living animal, e.g., as the complete gene, a transcript, or a cDNA. This polynucleotide can be part of a vector or inserted into a chromosome (by specific gene-targeting or by random integration at a position other than its normal position) and still be isolated in that it is not in a form that is found in its natural environment. A polynucleotide, polypeptide, etc., of the present invention can also be substantially purified. By substantially purified, it is meant that polynucleotide or polypeptide is separated and is essentially free from other polynucleotides or polypeptides, i.e., the polynucleotide or polypeptide is the primary and active constituent. A polynucleotide can also be a recombinant molecule. By "recombinant," it is meant that the polynucleotide is an arrangement or form which does not occur in nature. For instance, a recombinant molecule comprising a promoter sequence would not encompass the naturally-occurring gene, but would include the promoter operably linked to a coding sequence not associated with it in nature, e.g., a reporter gene, or a truncation of the normal coding sequence.

The term "marker" is used herein to indicate a means for detecting or labeling a target. A marker can be a polynucleotide (usually referred to as a "probe"), polypeptide (e.g., an antibody conjugated to a detectable label), PNA, or any effective material.

The topic headings set forth above are meant as guidance where certain information can be found in the application, but are not intended to be the only source in the application where information on such topic can be found.

Reference materials

For other aspects of the polynucleotides, reference is made to standard textbooks of molecular biology. See, e.g., Hames et al., *Polynucleotide Hybridization*, IL Press, 1985; Davis et al., *Basic Methods in Molecular Biology*, Elsevir Sciences Publishing, Inc., New York, 1986; Sambrook et al., *Molecular Cloning*, CSH Press, 1989; Howe, *Gene Cloning and Manipulation*, Cambridge University Press, 1995; Ausubel et al., *Current Protocols in Molecular Biology*, John Wiley & Sons, Inc., 1994–1998.

The preceding description, utilize the present invention to its fullest extent. The preceding preferred specific embodiments are, therefore, to be construed as merely illustrative, and not limiting the remainder of the disclosure in any way whatsoever. The entire disclosure of all applications, patents and publications, cited above and in the figures are hereby incorporated by reference in their entirety.

TABLE 1

| Variant | Nucleotide change |
|---|---|
| Pro18Ala | 52C > G |
| 86insA | |
| Val60Leu | 178G > T |
| Ala64Ser | 190G > T |
| Arg67Gln | 200G > A |
| Phe76Tyr | 227T > A |
| Asp84Glu | 252C > A |
| Ala81Pro | 241G > C |
| Val92Met | 274G > A |
| Thr95Met | 284C > T |
| Val97Ile | 289G > A |
| Ala103Val | 308C > T |
| Gly104Ser | 310G > A |
| Leu106Gln | 317T > A |
| Leu106Leu | 318G > A |
| Arg142His | 425G > A |
| Arg151Cys | 451C > T |
| Arg151Arg | 453C > G |
| Ile155Thr | 464T > C |
| Arg160Trp | 478C > T |
| Arg163Gln | 488G > A |
| Val173del | |
| Val174Ile | 520G > A |
| 537insC | |
| Pro230Leu | 689C > T |
| Pro230Pro | 690G > A |
| Gln233Gln | 699G > A |
| His260Pro | 779A > C |
| Ile264Ile | 792C > T |
| Cys273Cys | 819C > T |
| Lys278Glu | 832A > G |

TABLE 1-continued

| Variant | Nucleotide change |
|---|---|
| Asn279Ser | 836A > G |
| Asn279Lys | 837C > A |
| Ile287Met | 861C > G |
| Asp294His | 8800 > C |
| Phe300Phe | 900C > T |
| Thr314Thr | 942A > G |
| Ser316Ser | 948C > T |

TABLE 2

| | Allele Frequency. % | | Stimulation |
| Allele | White Populations | Individuals With Red Hair | at cAMP Production |
|---|---|---|---|
| Wild type | 53 | 23 | +++ |
| Val60Leu4† | 10 | 3 | + |
| Ala64Ser | <1 | 1 | NA |
| Lys65Asn | <1 | <1 | NA |
| Arg67Gln | 0‡ | 0 | NA |
| Arg67Val | 0‡ | 0 | NA |
| Phe76Tyr | <1 | <1 | NA |
| Asp84Glu | 1 | 3 | +++ |
| Asn91Asp | <1 | 0 | NA |
| Val92Leu | <1 | 1 | NA |
| Val92Met | 8 | 8 | +++ |
| Thr95Met | <1 | 1 | NA |
| Val97/Ile | <1 | <1 | NA |
| Ala103Val | <1 | <1 | NA |
| Leu106Gln | <1 | <1 | NA |
| Arg142His | <1 | 1 | — |
| Arg151Cys§ | 8 | 25 | — |
| Ile155Thr | <1 | <1 | NA |
| Arg160Trp§ | 7 | 19 | — |
| Arg163Gln | 4‖ | <1 | NA |
| Ile287Met | 0‡ | 0 | NA |
| Asp294His§ | 4 | 13 | — |
| Ala299Thr | <1 | 1 | NA |
| ins29¶ | <1 | <1 | — |
| ins179¶ | <1 | <1 | — |

"Several synonymous variants have also been described, including Leu106Leu, Leu158Leu, Gln233Gln, Cys273Gys, Phe300Phe, Thr314Thr, andSer316Ser. MC1-R indicates melanocortin-1 receptor; cAMP, cyclic adenosine monophosphate; triple plus sign, significant stimulation (same aswild type); single plus sign, minimal stimulation; NA, data not available; and minus sign, no stimulation (nonfunctional receptor)

†Possible association with blond/fair hair.

‡Present in <1% of East/Southeast Asians.

§Strong association with red hair, fair skin, and poor tanning ability; recent work also shows an association with cutaneous melanoma and non-melanoma skin cancer.

‖Present in >70% of East/Southeast Asian and Native Americans.

¶ins indicates insertion; these single-nucleotide insertion mutations produce frameshifts that result in a prematurely terminated, nonfunctionina

The invention claimed is:

1. An isolated polynucleotide comprising, a polynucleotide sequence coding without interruption for a human MCR-1C (melanocortin receptor 1C), or the complete complement to said polynucleotide sequence, said MCR-1C having 84% or more amino acid sequence identity along its entire length to the sequence consisting of amino acids 1–316 of SEQ ID NO 2, and 90% or more amino acid sequence identity along its entire length to the sequence consisting of amino acids 317–398 of SEQ ID NO 2, and which has ligand-binding activity, G-protein binding activity, or cAMP production activity, wherein said polynucleotide sequence coding for human MCR-1C hybridizes under high stringency conditions to the complete complement of SEQ ID NO: 1 from nucleotide position 342–1535, and the conditions comprise overnight incubation in 5X SSC, 0.5% SDS, 100 µ/ml denatured salmon sperm DNA and 50% formamide, at 42° C. followed by washing in 0.1% SSC and 0.1% SDS for 30 min at 65° C.

2. An isolated polynucleotide of claim 1, said MCR-1C having 90% or more amino acid sequence identity along its entire length to the sequence consisting of amino acids 1–316 of SEQ ID NO 2, and 95% or more amino acid sequence identity along its entire length to the sequence consisting from amino acids 317–398 of SEQ ID NO 2.

3. An isolated polynucleotide of claim 1, which codes for the human MCR-1C of SEQ ID NO 2.

4. An isolated polynucleotide of claim 1, which comprises the polynucleotide sequence set forth in SEQ ID NO 1.

5. An isolated polynucleotide of claim 1, which codes for the human MCR-1C of SEQ ID NO 3.

6. An isolated polynucleotide comprising a polynucleotide sequence coding for amino acids 367–398 of SEQ ID NO 2.

7. A method of expressing a human MCR-1C polynucleotide in a host cell, comprising
(a) introducing into a host cell the polynucleotide of claim 1 coding for a human MCR-1C polypeptide, wherein said polynucleotide is operably linked to a promoter, and
(b) culturing said host cell under conditions to achieve expression of said polynucleotide and production of said MCR-1C polypeptide.

8. A method of expressing a human MCR-1C polynucleotide in a host cell, comprising
(a) introducing into a host cell the polynucleotide of claim 2 coding for a human MCR-1C polypeptide, wherein said polynucleotide is operably linked to a promoter, and
(b) culturing said host cell under conditions to achieve expression of said polynucleotide and production of said MCR-1C polypeptide.

9. A method of expressing a human MCR-1C polynucleotide in a host cell, comprising
(a) introducing into a host cell the polynucleotide of claim 3 coding for a human MCR-1C polypeptide, wherein said polynucleotide is operably linked to a promoter, and
(b) culturing said host cell under conditions to achieve expression of said polynucleotide and production of said MCR-1C polypeptide.

10. A method of expressing a human MCR-1C polynucleotide in a host cell, comprising
(a) introducing into a host cell the polynucleotide of claim 4 coding for a human MCR-1C polypeptide, wherein said polynucleotide is operably linked to a promoter, and
(b) culturing said host cell under conditions to achieve expression of said polynucleotide and production of said MCR-1C polypeptide.

11. A method of expressing a human MCR-1C polynucleotide in a host cell, comprising
(a) introducing into a host cell the polynucleotide of claim 5 coding for a human MCR-1C polypeptide, wherein said polynucleotide is operably linked to a promoter, and
(b) culturing said host cell under conditions to achieve expression of said polynucleotide and production of said MCR-1C polypeptide.

12. An isolated polynucleotide of claim 1, which codes for the human MCR-1C of SEQ ID NO:4.

13. An isolated polynucleotide of claim 1, which codes for the human MCR-1C of SEQ ID NO:5.

14. An isolated polynucleotide of claim 6, consisting of a polynucleotide sequence coding for amino acid 367–398 of SEQ ID NO:2.

* * * * *

SEQUENCE LISTING

<160> NUMBER OF SEQ ID NOS: 13

<210> SEQ ID NO 1
<211> LENGTH: 3456
<212> TYPE: DNA
<213> ORGANISM: Homo sapiens
<220> FEATURE:
<221> NAME/KEY: CDS
<222> LOCATION: (342)..(1535)

<400> SEQUENCE: 1

| | |
|---|---|
| ggacggtcca gaggtgtcga aatgtcctgg ggacctgagc agcagccacc agggaagagg | 60 |
| cagggaggga gctgaggacc aggcttggtt gtgagaatcc ctgagcccag gcggtagatg | 120 |
| ccaggaggtg tctggactgg ctgggccatg cctgggctga cctgtccagc cagggagagg | 180 |
| gtgtgagggc agatctgggg gtgcccagat ggaaggaggc aggcatgggg gacacccaag | 240 |
| gcccctggc agcaccatga actaagcagg acacctggag gggaagaact gtggggacct | 300 |
| ggaggcctcc aacgactcct tcctgcttcc tggacaggac t atg gct gtg cag gga | 356 |
| Met Ala Val Gln Gly | |
| 1 5 | |

| | |
|---|---|
| tcc cag aga aga ctt ctg ggc tcc ctc aac tcc acc ccc aca gcc atc | 404 |
| Ser Gln Arg Arg Leu Leu Gly Ser Leu Asn Ser Thr Pro Thr Ala Ile | |
| 10 15 20 | |

| | |
|---|---|
| ccc cag ctg ggg ctg gct gcc aac cag aca gga gcc cgg tgc ctg gag | 452 |
| Pro Gln Leu Gly Leu Ala Ala Asn Gln Thr Gly Ala Arg Cys Leu Glu | |
| 25 30 35 | |

| | |
|---|---|
| gtg tcc atc tct gac ggg ctc ttc ctc agc ctg ggg ctg gtg agc ttg | 500 |
| Val Ser Ile Ser Asp Gly Leu Phe Leu Ser Leu Gly Leu Val Ser Leu | |
| 40 45 50 | |

| | |
|---|---|
| gtg gag aac gcg ctg gtg gtg gcc acc atc gcc aag aac cgg aac ctg | 548 |
| Val Glu Asn Ala Leu Val Val Ala Thr Ile Ala Lys Asn Arg Asn Leu | |
| 55 60 65 | |

| | |
|---|---|
| cac tca ccc atg tac tgc ttc atc tgc tgc ctg gcc ttg tcg gac ctg | 596 |
| His Ser Pro Met Tyr Cys Phe Ile Cys Cys Leu Ala Leu Ser Asp Leu | |
| 70 75 80 85 | |

| | |
|---|---|
| ctg gtg agc ggg agc aac gtg ctg gag acg gcc gtc atc ctc ctg ctg | 644 |
| Leu Val Ser Gly Ser Asn Val Leu Glu Thr Ala Val Ile Leu Leu Leu | |
| 90 95 100 | |

| | |
|---|---|
| gag gcc ggt gca ctg gtg gcc cgg gct gcg gtg ctg cag cag ctg gac | 692 |
| Glu Ala Gly Ala Leu Val Ala Arg Ala Ala Val Leu Gln Gln Leu Asp | |
| 105 110 115 | |

| | |
|---|---|
| aat gtc act gac gtg atc acc tgc agc tcc atg ctg tcc agc ctc tgc | 740 |
| Asn Val Thr Asp Val Ile Thr Cys Ser Ser Met Leu Ser Ser Leu Cys | |
| 120 125 130 | |

| | |
|---|---|
| ttc ctg ggc gcc atc gcc gtg gac cgc tac atc tcc atc ttc tac gca | 788 |
| Phe Leu Gly Ala Ile Ala Val Asp Arg Tyr Ile Ser Ile Phe Tyr Ala | |
| 135 140 145 | |

| | |
|---|---|
| ctg cgc tac cac agc atc gtg acc ctg ccg cgg gcg cgg cga gcc gtt | 836 |
| Leu Arg Tyr His Ser Ile Val Thr Leu Pro Arg Ala Arg Arg Ala Val | |
| 150 155 160 165 | |

| | |
|---|---|
| gcg gcc atc tgg gtg gcc agt gtc gtc ttc agc acg ctc ttc atc gcc | 884 |
| Ala Ala Ile Trp Val Ala Ser Val Val Phe Ser Thr Leu Phe Ile Ala | |
| 170 175 180 | |

| | |
|---|---|
| tac tac gac cac gtg gcc gtc ctg ctg tgc ctc gtg gtc ttc ttc ctg | 932 |
| Tyr Tyr Asp His Val Ala Val Leu Leu Cys Leu Val Val Phe Phe Leu | |
| 185 190 195 | |

| | |
|---|---|
| gct atg ctg gtg ctc atg gcc gtg ctg tac gtc cac atg ctg gcc cgg | 980 |
| Ala Met Leu Val Leu Met Ala Val Leu Tyr Val His Met Leu Ala Arg | |
| 200 205 210 | |

-continued

```
gcc tgc cag cac gcc cag ggc atc gcc cgg ctc cac aag agg cag cgc     1028
Ala Cys Gln His Ala Gln Gly Ile Ala Arg Leu His Lys Arg Gln Arg
    215                 220                 225
ccg gtc cac cag ggc ttt ggc ctt aaa ggc gct gtc acc ctc acc atc     1076
Pro Val His Gln Gly Phe Gly Leu Lys Gly Ala Val Thr Leu Thr Ile
230                 235                 240                 245
ctg ctg ggc att ttc ttc ctc tgc tgg ggc ccc ttc ttc ctg cat ctc     1124
Leu Leu Gly Ile Phe Phe Leu Cys Trp Gly Pro Phe Phe Leu His Leu
                250                 255                 260
aca ctc atc gtc ctc tgc ccc gag cac ccc acg tgc ggc tgc atc ttc     1172
Thr Leu Ile Val Leu Cys Pro Glu His Pro Thr Cys Gly Cys Ile Phe
            265                 270                 275
aag aac ttc aac ctc ttt ctc gcc ctc atc atc tgc aat gcc atc atc     1220
Lys Asn Phe Asn Leu Phe Leu Ala Leu Ile Ile Cys Asn Ala Ile Ile
        280                 285                 290
gac ccc ctc atc tac gcc ttc cac agc cag gag ctc cgc agg acg ctc     1268
Asp Pro Leu Ile Tyr Ala Phe His Ser Gln Glu Leu Arg Arg Thr Leu
    295                 300                 305
aag gag gtg ctg aca tgc tcc tgc tct cag gac cgt gcc ctc gtc agc     1316
Lys Glu Val Leu Thr Cys Ser Cys Ser Gln Asp Arg Ala Leu Val Ser
310                 315                 320                 325
tgg gat gtg aag tct ctg ggt gga agt gtg tgc caa gag cta ctc cca     1364
Trp Asp Val Lys Ser Leu Gly Gly Ser Val Cys Gln Glu Leu Leu Pro
                330                 335                 340
cag cag ccc cag gag aag ggg ctt tgt gac cag aaa gct tca tcc aca     1412
Gln Gln Pro Gln Glu Lys Gly Leu Cys Asp Gln Lys Ala Ser Ser Thr
            345                 350                 355
gcc ttg cag cgg ctc ctg caa aag gag cct aga gga agg acg agc agg     1460
Ala Leu Gln Arg Leu Leu Gln Lys Glu Pro Arg Gly Arg Thr Ser Arg
        360                 365                 370
tgc agc agg gcc cca gtc ccc tcc act ctt gac gct gtc cta gct gca     1508
Cys Ser Arg Ala Pro Val Pro Ser Thr Leu Asp Ala Val Leu Ala Ala
    375                 380                 385
gaa gag gcg ggt tcc cag cct tcc ctg tgaccacatg tgacctcagc           1555
Glu Glu Ala Gly Ser Gln Pro Ser Leu
390                 395
cgggacacat ccctttgctg gccctggccc tgagtccctc cagccatgat gagccgtgaa   1615
tgggaccatc cctgtccact ctgagatgcc tggaaggggg ctcagtgcag agactgagca   1675
ctcagtcagc ccccttcctg ggacaggctc aatggaggct gcagggccat cagccgactc   1735
ctacgcaggc tcagtcagca gccccctggc cagccccacc cctgactgcc ggcctcagaa   1795
ctgggagctg cttcctggca gggcccgcct ctgctgggag accggacgtt ctgggaagtc   1855
atcagtgatg agcatggcat cgaccccagc ggcaactacg tgggcgactc ggacttgcag   1915
ctggagcgga tcagcgtcta ctacaacgag gcctcttctc acaagtacgt gcctcgagcc   1975
attctggtgg acctggaacc cggaaccatg gacagtgtcc gctcaggggc ctttggacat   2035
ctcttcaggc ctgacaattt catctttggt cagagtgggg ccggcaacaa ctgggccaag   2095
ggtcactaca cggagggggc ggagctggtg gattcggtcc tggatgtggt gcggaaggag   2155
tgtgaaaact gcgactgcct gcagggcttc cagctgaccc actcgctggg gggcggcacg   2215
ggctccggca tgggcacgtt gctcatcagc aaggtgcgtg aggagtatcc cgaccgcatc   2275
atgaacacct tcagcgtcgt gccctcaccc aaggtgtcag acacggtggt ggagccctac   2335
aacgccacgc tgtccatcca ccagctggtg gagaacacgg atgagaccta ctgcatcgac   2395
aacgaggcgc tctacgacat ctgcttccgc accctcaagc tggccacgcc cacctacggg   2455
gacctcaacc acctggtatc ggccaccatg agcggagtca ccacctcctt gcgcttcccg   2515
```

```
ggccagctca acgctgacct gcgcaagctg gccgtcaaca tggtgccctt cccgcgcctg      2575
cacttcttca tgcccggctt cgccccctc acagcccggg gcagccagca gtaccgggcc       2635
ctgaccgtgc ccgagctcac ccagcagatg ttcgatgcca gaacatgat ggccgcctgc       2695 gacccgcgcc acggccgcta cctgacggtg gccaccgtgt tccggggccg catgtccatg     2755
aaggaggtgg acgagcagat gctggccatc cagagcaaga acagcagcta cttcgtggag     2815
tggatcccca caacgtgaa ggtggccgtg tgtgacatcc cgccccgcgg cctcaagatg      2875
tcctccacct tcatcgggaa cagcacggcc atccaggagc tgttcaagcg catctccgag     2935
cagttcacgg ccatgttccg gcgcaaggcc ttcctgcact ggtacacggg cgagggcatg     2995
gacgagatgg agttcaccga ggccgagagc aacatgaacg acctggtgtc cgagtaccag    3055
cagtaccagg acgccacggc cgaggaagag ggcgagatgt acgaagacga cgaggaggag     3115
tcggaggccc agggccccaa gtgaagctgc tcgcagctgg agtgagaggc aggtggcggc    3175
cggggccgaa gccagcagtg tctaaacccc cggagccatc ttgctgccga cacccctgctt   3235 tccctcgcc ctagggctcc cttgccgccc tcctgcagta tttatggcct cgtcctcccc      3295
acctaggcca cgtgtgagct gctcctgtct ctgtcttatt gcagctccag gcctgacgtt     3355
ttacggtttt gttttttact ggtttgtgtt tatattttcg gggatactta ataaatctat     3415
tgctgtcaga taaaaaaaaa aaaaaaaaa aaaaaaaaa a                           3456
```

<210> SEQ ID NO 2
<211> LENGTH: 398
<212> TYPE: PRT
<213> ORGANISM: Homo sapiens

<400> SEQUENCE: 2

Met Ala Val Gln Gly Ser Gln Arg Arg Leu Leu Gly Ser Leu Asn Ser
1               5                   10                  15

Thr Pro Thr Ala Ile Pro Gln Leu Gly Leu Ala Ala Asn Gln Thr Gly
            20                  25                  30

Ala Arg Cys Leu Glu Val Ser Ile Ser Asp Gly Leu Phe Leu Ser Leu
        35                  40                  45

Gly Leu Val Ser Leu Val Glu Asn Ala Leu Val Val Ala Thr Ile Ala
    50                  55                  60

Lys Asn Arg Asn Leu His Ser Pro Met Tyr Cys Phe Ile Cys Cys Leu
65                  70                  75                  80

Ala Leu Ser Asp Leu Leu Val Ser Gly Ser Asn Val Leu Glu Thr Ala
                85                  90                  95

Val Ile Leu Leu Leu Glu Ala Gly Ala Leu Val Ala Arg Ala Ala Val
            100                 105                 110

Leu Gln Gln Leu Asp Asn Val Thr Asp Val Ile Thr Cys Ser Ser Met
        115                 120                 125

Leu Ser Ser Leu Cys Phe Leu Gly Ala Ile Ala Val Asp Arg Tyr Ile
    130                 135                 140

Ser Ile Phe Tyr Ala Leu Arg Tyr His Ser Ile Val Thr Leu Pro Arg
145                 150                 155                 160

Ala Arg Arg Ala Val Ala Ala Ile Trp Val Ala Ser Val Val Phe Ser
                165                 170                 175

Thr Leu Phe Ile Ala Tyr Tyr Asp His Val Ala Val Leu Leu Cys Leu
            180                 185                 190

Val Val Phe Phe Leu Ala Met Leu Val Leu Met Ala Val Leu Tyr Val
        195                 200                 205

-continued

```
His Met Leu Ala Arg Ala Cys Gln His Ala Gln Gly Ile Ala Arg Leu
    210                 215                 220

His Lys Arg Gln Arg Pro Val His Gln Gly Phe Gly Leu Lys Gly Ala
225                 230                 235                 240

Val Thr Leu Thr Ile Leu Leu Gly Ile Phe Phe Leu Cys Trp Gly Pro
                245                 250                 255

Phe Phe Leu His Leu Thr Leu Ile Val Leu Cys Pro Glu His Pro Thr
            260                 265                 270

Cys Gly Cys Ile Phe Lys Asn Phe Asn Leu Phe Leu Ala Leu Ile Ile
        275                 280                 285

Cys Asn Ala Ile Ile Asp Pro Leu Ile Tyr Ala Phe His Ser Gln Glu
    290                 295                 300

Leu Arg Arg Thr Leu Lys Glu Val Leu Thr Cys Ser Cys Ser Gln Asp
305                 310                 315                 320

Arg Ala Leu Val Ser Trp Asp Val Lys Ser Leu Gly Gly Ser Val Cys
                325                 330                 335

Gln Glu Leu Leu Pro Gln Pro Gln Lys Gly Leu Cys Asp Gln
            340                 345                 350

Lys Ala Ser Ser Thr Ala Leu Gln Arg Leu Leu Gln Lys Glu Pro Arg
            355                 360                 365

Gly Arg Thr Ser Arg Cys Ser Arg Ala Pro Val Pro Ser Thr Leu Asp
370                 375                 380

Ala Val Leu Ala Ala Glu Glu Ala Gly Ser Gln Pro Ser Leu
385                 390                 395

<210> SEQ ID NO 3
<211> LENGTH: 398
<212> TYPE: PRT
<213> ORGANISM: Homo sapiens

<400> SEQUENCE: 3

Met Ala Val Gln Gly Ser Gln Arg Arg Leu Leu Gly Ser Leu Asn Ser
1               5                   10                  15

Thr Pro Thr Ala Ile Pro Gln Leu Gly Leu Ala Ala Asn Gln Thr Gly
                20                  25                  30

Ala Arg Cys Leu Glu Val Ser Ile Ser Asp Gly Leu Phe Leu Ser Leu
            35                  40                  45

Gly Leu Val Ser Leu Val Glu Asn Ala Leu Val Val Ala Thr Ile Ala
        50                  55                  60

Lys Asn Arg Asn Leu His Ser Pro Met Tyr Cys Phe Ile Cys Cys Leu
65                  70                  75                  80

Ala Leu Ser Asp Leu Leu Val Ser Gly Ser Asn Val Leu Glu Thr Ala
                85                  90                  95

Val Ile Leu Leu Leu Glu Ala Gly Ala Leu Val Ala Arg Ala Ala Val
            100                 105                 110

Leu Gln Gln Leu Asp Asn Val Thr Asp Val Ile Thr Cys Ser Ser Met
        115                 120                 125

Leu Ser Ser Leu Cys Phe Leu Gly Ala Ile Ala Val Asp Arg Tyr Ile
    130                 135                 140

Ser Ile Phe Tyr Ala Leu Arg Tyr His Ser Ile Val Thr Leu Pro Arg
145                 150                 155                 160

Ala Arg Gln Ala Val Ala Ala Ile Trp Val Ala Ser Val Val Phe Ser
                165                 170                 175

Thr Leu Phe Ile Ala Tyr Tyr Asp His Val Ala Val Leu Leu Cys Leu
            180                 185                 190
```

-continued

Val Val Phe Leu Ala Met Leu Val Leu Met Ala Val Leu Tyr Val
           195                 200                 205

His Met Leu Ala Arg Ala Cys Gln His Ala Gln Gly Ile Ala Arg Leu
210                 215                 220

His Lys Arg Gln Arg Pro Val His Gln Gly Phe Gly Leu Lys Gly Ala
225                 230                 235                 240

Val Thr Leu Thr Ile Leu Leu Gly Ile Phe Phe Leu Cys Trp Gly Pro
               245                 250                 255

Phe Phe Leu His Leu Thr Leu Ile Val Leu Cys Pro Glu His Pro Thr
               260                 265                 270

Cys Gly Cys Ile Phe Lys Asn Phe Asn Leu Phe Leu Ala Leu Ile Ile
               275                 280                 285

Cys Asn Ala Ile Ile Asp Pro Leu Ile Tyr Ala Phe His Ser Gln Glu
               290                 295                 300

Leu Arg Arg Thr Leu Lys Glu Val Leu Thr Cys Ser Cys Ser Gln Asp
305                 310                 315                 320

Arg Ala Leu Val Ser Trp Asp Val Lys Ser Leu Gly Gly Ser Val Cys
                   325                 330                 335

Gln Glu Leu Leu Pro Gln Pro Gln Glu Lys Gly Leu Cys Asp Gln
                   340                 345                 350

Lys Ala Ser Ser Thr Ala Leu Gln Arg Leu Leu Gln Lys Glu Pro Arg
                   355                 360                 365

Gly Arg Thr Ser Arg Cys Ser Arg Ala Pro Val Pro Ser Thr Leu Asp
370                 375                 380

Ala Val Leu Ala Ala Glu Glu Ala Gly Ser Gln Pro Ser Leu
385                 390                 395

<210> SEQ ID NO 4
<211> LENGTH: 398
<212> TYPE: PRT
<213> ORGANISM: Homo sapiens

<400> SEQUENCE: 4

Met Ala Val Gln Gly Ser Gln Arg Arg Leu Leu Gly Ser Leu Asn Ser
1               5                   10                  15

Thr Pro Thr Ala Ile Pro Gln Leu Gly Leu Ala Ala Asn Gln Thr Gly
                20                  25                  30

Ala Arg Cys Leu Glu Val Ser Ile Ser Asp Gly Leu Phe Leu Ser Leu
            35                  40                  45

Gly Leu Val Ser Leu Val Glu Asn Ala Leu Val Val Ala Thr Ile Ala
        50                  55                  60

Lys Asn Arg Asn Leu His Ser Pro Met Tyr Cys Phe Ile Cys Cys Leu
65                  70                  75                  80

Ala Leu Ser Asp Leu Leu Val Ser Gly Ser Asn Val Leu Glu Thr Ala
                85                  90                  95

Val Ile Leu Leu Leu Glu Ala Gly Ala Leu Val Ala Arg Ala Ala Val
            100                 105                 110

Leu Gln Gln Leu Asp Asn Val Ile Asp Val Ile Thr Cys Ser Ser Met
        115                 120                 125

Leu Ser Ser Leu Cys Phe Leu Gly Ala Ile Ala Val Asp Arg Tyr Ile
    130                 135                 140

Ser Ile Phe Tyr Ala Leu Arg Tyr His Ser Ile Val Thr Leu Pro Arg
145                 150                 155                 160

Ala Arg Arg Ala Val Ala Ala Ile Trp Val Ala Ser Val Phe Ser
                165                 170                 175

```
Thr Leu Phe Ile Ala Tyr Tyr Asp His Val Ala Val Leu Leu Cys Leu
            180                 185                 190

Val Val Phe Leu Ala Met Leu Val Leu Met Ala Val Leu Tyr Val
        195                 200                 205

His Met Leu Ala Arg Ala Cys Gln His Ala Gln Gly Ile Ala Arg Leu
210                 215                 220

His Lys Arg Gln Arg Pro Val His Gln Gly Phe Gly Leu Lys Gly Ala
225                 230                 235                 240

Val Thr Leu Thr Ile Leu Leu Gly Ile Phe Phe Leu Cys Trp Gly Pro
                245                 250                 255

Phe Phe Leu His Leu Thr Leu Ile Val Leu Cys Pro Glu His Pro Thr
            260                 265                 270

Cys Gly Cys Ile Phe Lys Asn Phe Asn Leu Phe Leu Ala Leu Ile Ile
        275                 280                 285

Cys Asn Ala Ile Ile Asp Pro Leu Ile Tyr Ala Phe His Ser Gln Glu
290                 295                 300

Leu Arg Arg Thr Leu Lys Glu Val Leu Thr Cys Ser Cys Ser Gln Asp
305                 310                 315                 320

Arg Ala Leu Val Ser Trp Asp Val Lys Ser Leu Gly Gly Ser Val Cys
                325                 330                 335

Gln Glu Leu Leu Pro Gln Gln Pro Gln Glu Lys Gly Leu Cys Asp Gln
            340                 345                 350

Lys Ala Ser Ser Thr Ala Leu Gln Arg Leu Leu Gln Lys Glu Pro Arg
        355                 360                 365

Gly Arg Thr Ser Arg Cys Ser Arg Ala Pro Val Pro Ser Thr Leu Asp
370                 375                 380

Ala Val Leu Ala Ala Glu Glu Ala Gly Ser Gln Pro Ser Leu
385                 390                 395

<210> SEQ ID NO 5
<211> LENGTH: 398
<212> TYPE: PRT
<213> ORGANISM: Homo sapiens

<400> SEQUENCE: 5

Met Ala Val Gln Gly Ser Gln Arg Arg Leu Leu Gly Ser Leu Asn Ser
1               5                   10                  15

Thr Pro Thr Ala Ile Pro Gln Leu Gly Leu Ala Ala Asn Gln Thr Gly
            20                  25                  30

Ala Arg Cys Leu Glu Val Ser Ile Ser Asp Gly Leu Phe Leu Ser Leu
        35                  40                  45

Gly Leu Val Ser Leu Val Glu Asn Ala Leu Val Val Ala Thr Ile Ala
    50                  55                  60

Lys Asn Arg Asn Leu His Ser Pro Met Tyr Cys Phe Ile Cys Cys Leu
65                  70                  75                  80

Ala Leu Ser Asp Leu Leu Val Ser Gly Ser Asn Val Leu Glu Thr Ala
                85                  90                  95

Val Ile Leu Leu Leu Glu Ala Gly Ala Leu Val Ala Arg Ala Ala Val
            100                 105                 110

Leu Gln Gln Leu Asp Asn Val Ile Asp Val Ile Thr Cys Ser Ser Met
        115                 120                 125

Leu Ser Ser Leu Cys Phe Leu Gly Ala Ile Ala Val Asp Arg Tyr Ile
    130                 135                 140

Ser Ile Phe Tyr Ala Leu Arg Tyr His Ser Ile Val Thr Leu Pro Arg
145                 150                 155                 160
```

```
Ala Arg Gln Ala Val Ala Ala Ile Trp Val Ala Ser Val Val Phe Ser
                165                 170                 175

Thr Leu Phe Ile Ala Tyr Tyr Asp His Val Ala Val Leu Leu Cys Leu
            180                 185                 190

Val Val Phe Phe Leu Ala Met Leu Val Leu Met Ala Val Leu Tyr Val
        195                 200                 205

His Met Leu Ala Arg Ala Cys Gln His Ala Gln Gly Ile Ala Arg Leu
    210                 215                 220

His Lys Arg Gln Arg Pro Val His Gln Gly Phe Gly Leu Lys Gly Ala
225                 230                 235                 240

Val Thr Leu Thr Ile Leu Leu Gly Ile Phe Phe Leu Cys Trp Gly Pro
                245                 250                 255

Phe Phe Leu His Leu Thr Leu Ile Val Leu Cys Pro Glu His Pro Thr
            260                 265                 270

Cys Gly Cys Ile Phe Lys Asn Phe Asn Leu Phe Leu Ala Leu Ile Ile
        275                 280                 285

Cys Asn Ala Ile Ile Asp Pro Leu Ile Tyr Ala Phe His Ser Gln Glu
    290                 295                 300

Leu Arg Arg Thr Leu Lys Glu Val Leu Thr Cys Ser Cys Ser Gln Asp
305                 310                 315                 320

Arg Ala Leu Val Ser Trp Asp Val Lys Ser Leu Gly Gly Ser Val Cys
                325                 330                 335

Gln Glu Leu Leu Pro Gln Pro Gln Glu Lys Gly Leu Cys Asp Gln
            340                 345                 350

Lys Ala Ser Ser Thr Ala Leu Gln Arg Leu Leu Gln Lys Glu Pro Arg
        355                 360                 365

Gly Arg Thr Ser Arg Cys Ser Arg Ala Pro Val Pro Ser Thr Leu Asp
    370                 375                 380

Ala Val Leu Ala Ala Glu Glu Ala Gly Ser Gln Pro Ser Leu
385                 390                 395

<210> SEQ ID NO 6
<211> LENGTH: 317
<212> TYPE: PRT
<213> ORGANISM: Homo sapiens

<400> SEQUENCE: 6

Met Ala Val Gln Gly Ser Gln Arg Arg Leu Leu Gly Ser Leu Asn Ser
1               5                   10                  15

Thr Pro Thr Ala Ile Pro Gln Leu Gly Leu Ala Ala Asn Gln Thr Gly
            20                  25                  30

Ala Arg Cys Leu Glu Val Ser Ile Ser Asp Gly Leu Phe Leu Ser Leu
        35                  40                  45

Gly Leu Val Ser Leu Val Glu Asn Ala Leu Val Val Ala Thr Ile Ala
    50                  55                  60

Lys Asn Arg Asn Leu His Ser Pro Met Tyr Cys Phe Ile Cys Cys Leu
65                  70                  75                  80

Ala Leu Ser Asp Leu Leu Val Ser Gly Ser Asn Val Leu Glu Thr Ala
                85                  90                  95

Val Ile Leu Leu Leu Glu Ala Gly Ala Leu Val Ala Arg Ala Ala Val
            100                 105                 110

Leu Gln Gln Leu Asp Asn Val Ile Asp Val Ile Thr Cys Ser Ser Met
        115                 120                 125

Leu Ser Ser Leu Cys Phe Leu Gly Ala Ile Ala Val Asp Arg Tyr Ile
    130                 135                 140
```

```
Ser Ile Phe Tyr Ala Leu Arg Tyr His Ser Ile Val Thr Leu Pro Arg
145                 150                 155                 160

Ala Arg Gln Ala Val Ala Ile Trp Val Ala Ser Val Val Phe Ser
                165                 170                 175

Thr Leu Phe Ile Ala Tyr Tyr Asp His Val Ala Val Leu Leu Cys Leu
            180                 185                 190

Val Val Phe Phe Leu Ala Met Leu Val Leu Met Ala Val Leu Tyr Val
        195                 200                 205

His Met Leu Ala Arg Ala Cys Gln His Ala Gln Gly Ile Ala Arg Leu
210                 215                 220

His Lys Arg Gln Arg Pro Val His Gln Gly Phe Gly Leu Lys Gly Ala
225                 230                 235                 240

Val Thr Leu Thr Ile Leu Leu Gly Ile Phe Phe Leu Cys Trp Gly Pro
                245                 250                 255

Phe Phe Leu His Leu Thr Leu Ile Val Leu Cys Pro Glu His Pro Thr
            260                 265                 270

Cys Gly Cys Ile Phe Lys Asn Phe Asn Leu Phe Leu Ala Leu Ile Ile
        275                 280                 285

Cys Asn Ala Ile Ile Asp Pro Leu Ile Tyr Ala Phe His Ser Gln Glu
290                 295                 300

Leu Arg Arg Thr Leu Lys Glu Val Leu Thr Cys Ser Trp
305                 310                 315

<210> SEQ ID NO 7
<211> LENGTH: 382
<212> TYPE: PRT
<213> ORGANISM: Homo sapiens

<400> SEQUENCE: 7

Met Ala Val Gln Gly Ser Gln Arg Arg Leu Leu Gly Ser Leu Asn Ser
1               5                   10                  15

Thr Pro Thr Ala Ile Pro Gln Leu Gly Leu Ala Ala Asn Gln Thr Gly
                20                  25                  30

Ala Arg Cys Leu Glu Val Ser Ile Ser Asp Gly Leu Phe Leu Ser Leu
            35                  40                  45

Gly Leu Val Ser Leu Val Glu Asn Ala Leu Val Val Ala Thr Ile Ala
        50                  55                  60

Lys Asn Arg Asn Leu His Ser Pro Met Tyr Cys Phe Ile Cys Cys Leu
65                  70                  75                  80

Ala Leu Ser Asp Leu Leu Val Ser Gly Ser Asn Val Leu Glu Thr Ala
                85                  90                  95

Val Ile Leu Leu Leu Glu Ala Gly Ala Leu Val Ala Arg Ala Ala Val
            100                 105                 110

Leu Gln Gln Leu Asp Asn Val Ile Asp Val Ile Thr Cys Ser Ser Met
        115                 120                 125

Leu Ser Ser Leu Cys Phe Leu Gly Ala Ile Ala Val Asp Arg Tyr Ile
    130                 135                 140

Ser Ile Phe Tyr Ala Leu Arg Tyr His Ser Ile Val Thr Leu Pro Arg
145                 150                 155                 160

Ala Arg Arg Ala Val Ala Ala Ile Trp Val Ala Ser Val Val Phe Ser
                165                 170                 175

Thr Leu Phe Ile Ala Tyr Tyr Asp His Val Ala Val Leu Leu Cys Leu
            180                 185                 190

Val Val Phe Phe Leu Ala Met Leu Val Leu Met Ala Val Leu Tyr Val
        195                 200                 205
```

```
His Met Leu Ala Arg Ala Cys Gln His Ala Gln Gly Ile Ala Arg Leu
    210                 215                 220
His Lys Arg Gln Arg Pro Val His Gln Gly Phe Gly Leu Lys Gly Ala
225                 230                 235                 240
Val Thr Leu Thr Ile Leu Leu Gly Ile Phe Phe Leu Cys Trp Gly Pro
                245                 250                 255
Phe Phe Leu His Leu Thr Leu Ile Val Leu Cys Pro Glu His Pro Thr
                260                 265                 270
Cys Gly Cys Ile Phe Lys Asn Phe Asn Leu Phe Leu Ala Leu Ile Ile
            275                 280                 285
Cys Asn Ala Ile Ile Asp Pro Leu Ile Tyr Ala Phe His Ser Gln Glu
    290                 295                 300
Leu Arg Arg Thr Leu Lys Glu Val Leu Thr Cys Ser Cys Ser Gln Asp
305                 310                 315                 320
Arg Ala Leu Val Ser Trp Asp Val Lys Ser Leu Gly Gly Ser Val Cys
                325                 330                 335
Gln Glu Leu Leu Pro Gln Pro Gln Glu Lys Gly Leu Cys Asp Gln
            340                 345                 350
Lys Ala Ser Ser Thr Ala Leu Gln Arg Leu Leu Gln Lys Glu Val Lys
    355                 360                 365
Ser Leu Pro Gln Ala Lys Gly Pro Gly Leu Gln Glu Pro Pro
370                 375                 380

<210> SEQ ID NO 8
<211> LENGTH: 22
<212> TYPE: DNA
<213> ORGANISM: Homo sapiens

<400> SEQUENCE: 8
cctcatcatc tgcaatgcca tc                                            22

<210> SEQ ID NO 9
<211> LENGTH: 22
<212> TYPE: DNA
<213> ORGANISM: Homo sapiens

<400> SEQUENCE: 9
gctcgtcctt cctctaggct cc                                            22

<210> SEQ ID NO 10
<211> LENGTH: 22
<212> TYPE: DNA
<213> ORGANISM: Homo sapiens

<400> SEQUENCE: 10
aggaagcagc tcccagttct ga                                            22

<210> SEQ ID NO 11
<211> LENGTH: 50
<212> TYPE: DNA
<213> ORGANISM: Homo sapiens

<400> SEQUENCE: 11
cttccgcagc ggaaatggcg cgccgcccgg ggagggcggg agcagcgtcc               50

<210> SEQ ID NO 12
<211> LENGTH: 50
<212> TYPE: DNA
<213> ORGANISM: Homo sapiens

<400> SEQUENCE: 12
```

```
cctcaggctc tacaagatgc ctgaaaacac caacctctcc agggctcact          50
```

<210> SEQ ID NO 13
<211> LENGTH: 50
<212> TYPE: DNA
<213> ORGANISM: Homo sapiens

<400> SEQUENCE: 13

```
aacgactttt taaaacgcag agaaaagctc cattcttccc aggacctcag          50
```